(12) United States Patent
Schwab et al.

(10) Patent No.: US 9,867,939 B2
(45) Date of Patent: Jan. 16, 2018

(54) ADIPOSE TISSUE COMBINATIONS, DEVICES, AND USES THEREOF

(71) Applicant: Allergan, Inc., Irvine, CA (US)

(72) Inventors: Justin Schwab, Santa Barbara, CA (US); Mike Augarten, Goleta, CA (US); Darin Messina, Santa Barbara, CA (US); Jason Metzner, Covington, WA (US); Ethan Franklin, Goleta, CA (US)

(73) Assignee: Allergan, Inc., Irvine, CA (US)

( * ) Notice: Subject to any disclaimer, the term of this patent is extended or adjusted under 35 U.S.C. 154(b) by 707 days.

(21) Appl. No.: 14/204,796

(22) Filed: Mar. 11, 2014

(65) Prior Publication Data

US 2014/0276384 A1    Sep. 18, 2014

Related U.S. Application Data

(60) Provisional application No. 61/777,979, filed on Mar. 12, 2013, provisional application No. 61/778,014,
(Continued)

(51) Int. Cl.
*A61M 37/00* (2006.01)
*A61M 5/20* (2006.01)
(Continued)

(52) U.S. Cl.
CPC ............... *A61M 5/20* (2013.01); *A61K 35/35* (2013.01); *A61M 3/005* (2013.01); *A61M 5/19* (2013.01); *A61M 5/284* (2013.01); *C12N 5/0653* (2013.01); *A61M 1/0005* (2013.01); *A61M 1/0019* (2013.01); *A61M 1/0058* (2013.01);
(Continued)

(58) Field of Classification Search
CPC ..... A61K 35/35; A61M 3/005; A61M 1/0005; A61M 1/0019; A61M 1/0058; A61M 2202/08; A61M 5/148; A61M 5/1483; A61M 5/152; C12N 5/0653; B65D 83/0055; B65D 83/0066
See application file for complete search history.

(56) References Cited

U.S. PATENT DOCUMENTS 4,605,691 A    8/1986  Balazs et al.
4,627,444 A    12/1986 Brooker
(Continued)

FOREIGN PATENT DOCUMENTS

EP          1476202 B1    1/2009
WO    WO 2007095922 A1 *  8/2007    ......... B65D 83/0066
(Continued)

OTHER PUBLICATIONS

Laskowki, Sigismund; Machine English Translation of WO 2007/095922, Aug. 2007.*
(Continued)

*Primary Examiner* — Kevin C Sirmons
*Assistant Examiner* — Leah Swanson
(74) *Attorney, Agent, or Firm* — Nathan S. Smith; Claine Snow; McDermott Will & Emery LLP

(57) ABSTRACT

Described are devices, systems, and methods for processing adipose tissue for reintroduction into a body. In some embodiments, adipose tissue is mixed with an additive prior to reintroduction.

11 Claims, 6 Drawing Sheets

Related U.S. Application Data filed on Mar. 12, 2013, provisional application No. 61/778,099, filed on Mar. 12, 2013, provisional application No. 61/778,158, filed on Mar. 12, 2013, provisional application No. 61/778,210, filed on Mar. 12, 2013.

(51) Int. Cl.
| | |
|---|---|
| *A61M 3/00* | (2006.01) |
| *A61M 5/19* | (2006.01) |
| *C12N 5/077* | (2010.01) |
| *A61K 35/35* | (2015.01) |
| *A61M 5/28* | (2006.01) |
| *A61M 1/00* | (2006.01) |
| *A61M 5/31* | (2006.01) |

(52) U.S. Cl.
CPC ... *A61M 5/3145* (2013.01); *A61M 2005/3142* (2013.01); *A61M 2202/08* (2013.01); *A61M 2205/581* (2013.01); *A61M 2205/8206* (2013.01); *A61M 2209/086* (2013.01)

(56) References Cited

U.S. PATENT DOCUMENTS

| | | | |
|---|---|---|---|
| 4,898,572 A * | 2/1990 | Surugue nee Lasnier | A61M 1/0001 604/6.09 |
| 4,909,932 A | 3/1990 | Monnet | |
| 5,024,613 A * | 6/1991 | Vasconcellos | A61M 1/3627 604/319 |
| 5,137,181 A | 8/1992 | Keller | |
| 5,520,658 A | 5/1996 | Holm | |
| 5,584,815 A | 12/1996 | Pawelka et al. | |
| 5,650,317 A | 7/1997 | Chang et al. | |
| 5,716,404 A | 2/1998 | Vacanti | |
| 5,722,829 A | 3/1998 | Wilcox et al. | |
| 5,728,077 A * | 3/1998 | Williams | A61M 5/16818 604/246 |
| 5,814,511 A | 9/1998 | Chang et al. | |
| 5,853,388 A * | 12/1998 | Semel | A61J 1/2093 141/9 |
| 5,972,385 A | 10/1999 | Liu et al. | |
| 6,047,861 A | 4/2000 | Vidal et al. | |
| 6,082,364 A | 7/2000 | Balian et al. | |
| 6,083,912 A | 7/2000 | Khouri | |
| 6,129,761 A | 10/2000 | Hubbell et al. | |
| 6,171,610 B1 | 1/2001 | Vacanti et al. | |
| 6,176,396 B1 | 1/2001 | Hamada et al. | |
| 6,214,045 B1 | 4/2001 | Corbitt, Jr. et al. | |
| 6,239,105 B1 | 5/2001 | Brewitt et al. | |
| 6,316,247 B1 * | 11/2001 | Katz | A61L 27/3604 210/446 |
| 6,582,960 B1 | 6/2003 | Martin et al. | |
| 6,610,033 B1 | 8/2003 | Melanson et al. | |
| 6,638,308 B2 | 10/2003 | Corbitt | |
| 6,656,488 B2 | 12/2003 | Yi et al. | |
| 6,666,893 B2 | 12/2003 | Burg et al. | |
| 6,777,231 B1 | 8/2004 | Katz et al. | |
| 6,881,226 B2 | 4/2005 | Corbitt | |
| 6,916,603 B2 | 7/2005 | Baron et al. | |
| 6,991,652 B2 | 1/2006 | Burg et al. | |
| 7,015,037 B1 | 3/2006 | Furcht et al. | |
| 7,129,209 B2 | 10/2006 | Rhee et al. | |
| 7,285,266 B2 | 10/2007 | Voumakis et al. | |
| 7,316,822 B2 | 1/2008 | Binette et al. | |
| 7,390,484 B2 | 6/2008 | Fraser | |
| 7,445,793 B2 | 11/2008 | Niwa et al. | |
| 7,501,115 B2 | 3/2009 | Fraser et al. | |
| 7,514,075 B2 | 4/2009 | Hedrick et al. | |
| 7,560,276 B2 | 7/2009 | Harmon et al. | |
| 7,651,684 B2 | 1/2010 | Hedrick et al. | |
| 7,767,452 B2 | 8/2010 | Kleinsek et al. | |
| 7,799,767 B2 | 9/2010 | Lamberti et al. | |
| 7,875,296 B2 | 1/2011 | Binette et al. | |
| 8,053,423 B2 | 11/2011 | Lamberti et al. | |
| 8,066,691 B2 | 11/2011 | Khouri | |
| 8,137,705 B2 | 3/2012 | Doyle et al. | |
| 8,153,591 B2 | 4/2012 | Masters et al. | |
| 2003/0233067 A1 | 12/2003 | McIntosh et al. | |
| 2004/0092011 A1 | 5/2004 | Wilkison et al. | |
| 2005/0025755 A1 | 2/2005 | Hedrick | |
| 2005/0123895 A1 | 6/2005 | Freund | |
| 2005/0147562 A1 | 7/2005 | Hunter et al. | |
| 2007/0191781 A1 | 8/2007 | Richards et al. | |
| 2007/0251531 A1 | 11/2007 | Khouri | |
| 2008/0243028 A1 | 10/2008 | Howard et al. | |
| 2008/0299213 A2 | 12/2008 | Kleinsek | |
| 2008/0317718 A1 | 12/2008 | Yoshimura | |
| 2009/0098177 A1 | 4/2009 | Werkmeister et al. | |
| 2009/0123547 A1 | 5/2009 | Hill | |
| 2009/0124552 A1 | 5/2009 | Hill | |
| 2009/0131886 A1 | 5/2009 | Liu et al. | |
| 2009/0162415 A1 | 6/2009 | Huang et al. | |
| 2009/0246182 A1 | 10/2009 | Casteilla | |
| 2009/0312746 A1 | 12/2009 | Khouri | |
| 2009/0317367 A1 | 12/2009 | Chazenbalk | |
| 2010/0010627 A1 | 1/2010 | Matheny | |
| 2010/0279405 A1 * | 11/2010 | Peterson | C12M 47/04 435/366 |
| 2011/0070281 A1 | 3/2011 | Altman et al. | |
| 2011/0150823 A1 | 6/2011 | Huang | |
| 2011/0202014 A1 | 8/2011 | Mutzbauer | |
| 2011/0213336 A1 | 9/2011 | Cucin | |
| 2011/0282324 A1 | 11/2011 | Kurokawa et al. | |
| 2011/0282381 A1 | 11/2011 | Cronin et al. | |
| 2012/0010146 A1 | 1/2012 | Han et al. | |
| 2012/0076868 A1 | 3/2012 | Lamberti et al. | |
| 2012/0156265 A1 | 6/2012 | Binette et al. | |
| 2012/0209248 A1 | 8/2012 | Gurtner et al. | |
| 2014/0257179 A1 | 9/2014 | Schwab et al. | |

FOREIGN PATENT DOCUMENTS

| | | |
|---|---|---|
| WO | 2007124478 A2 | 11/2007 |
| WO | 2008063569 A1 | 5/2008 |
| WO | 2008148026 A1 | 12/2008 |
| WO | 2008148071 A2 | 12/2008 |
| WO | 2009003135 A1 | 12/2008 |
| WO | 2009047346 A1 | 4/2009 |
| WO | 2009085548 A2 | 7/2009 |
| WO | 2009103818 A1 | 8/2009 |
| WO | 2009115581 A2 | 9/2009 |
| WO | 2009155583 A1 | 12/2009 |
| WO | 2010026299 A1 | 3/2010 |
| WO | 2010127310 A1 | 11/2010 |
| WO | 2011072399 A1 | 6/2011 |
| WO | 2012006587 A2 | 1/2012 |
| WO | 2012019103 A2 | 2/2012 |

OTHER PUBLICATIONS

English Translation of WO 2007/095922.*
Kilroy, Gail et al., Cytokine Profile of Human Adipose-Derived Stem Cells: Expression of Angiogenic, Hematopoietic, and Pro-Inflammatory Factors, J. Cell. Physiol., 2007, 702-709, 212.
Rehman, Jalees et al., Secretion of Angiogenic and Antiapoptotic Factors by Human Adipose Stromal Cells, Circulation, 2004, 1292-1298, 109.
Yoshimura, Kotaro et al., Cell-Assisted Lipotransfer for Cosmetic Breast Augmentation: Supportive Use of Adipose-Derived Stem/Stromal Cells, Aesth. Plast. Surg., 2008, 48-55, 32.
Yoshimura, Kotaro et al., Cell-Assisted Lipotransfer for Facial Lipoatrophy: Effects of Clinical Use of Adipose-Derived Stem Cells, Dermatol. Surg., 2008, 1178-1185, 34.

(56) References Cited

OTHER PUBLICATIONS

Yoshimura, Kotaro et al., Characterization of Freshly Isolated and Cultured Cells Derived From the Fatty and Fluid Portions of Liposuction Aspirates, J Cell Physiol, 2006, 1011-1041, 208.

* cited by examiner

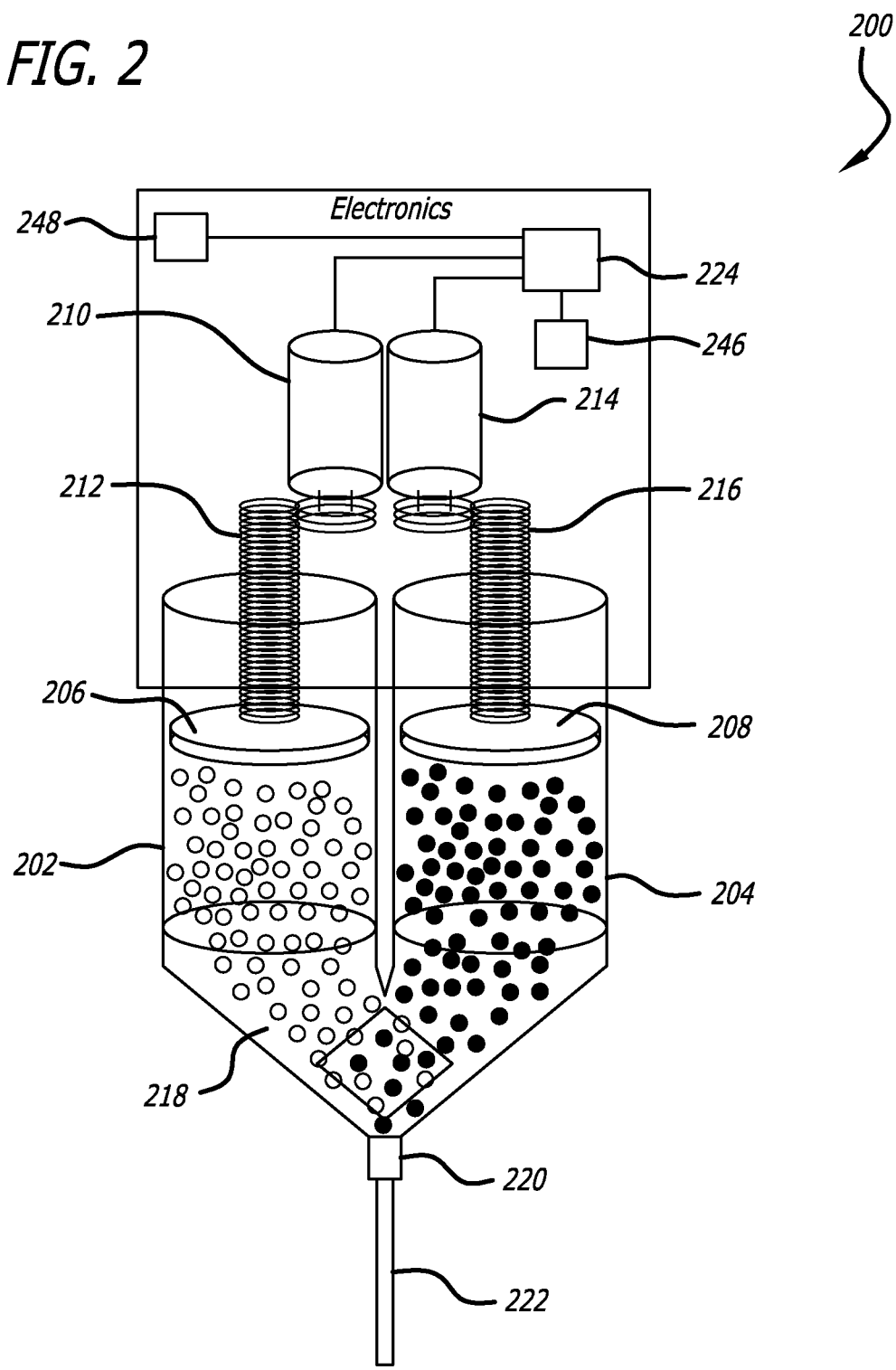

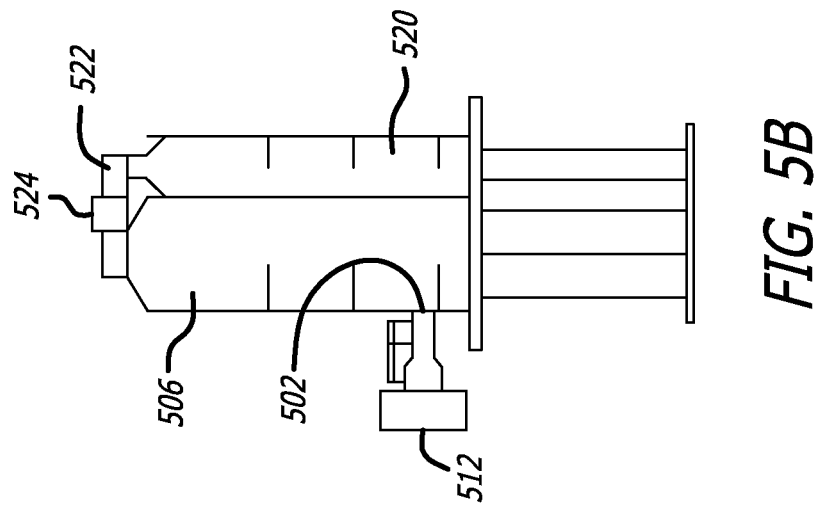
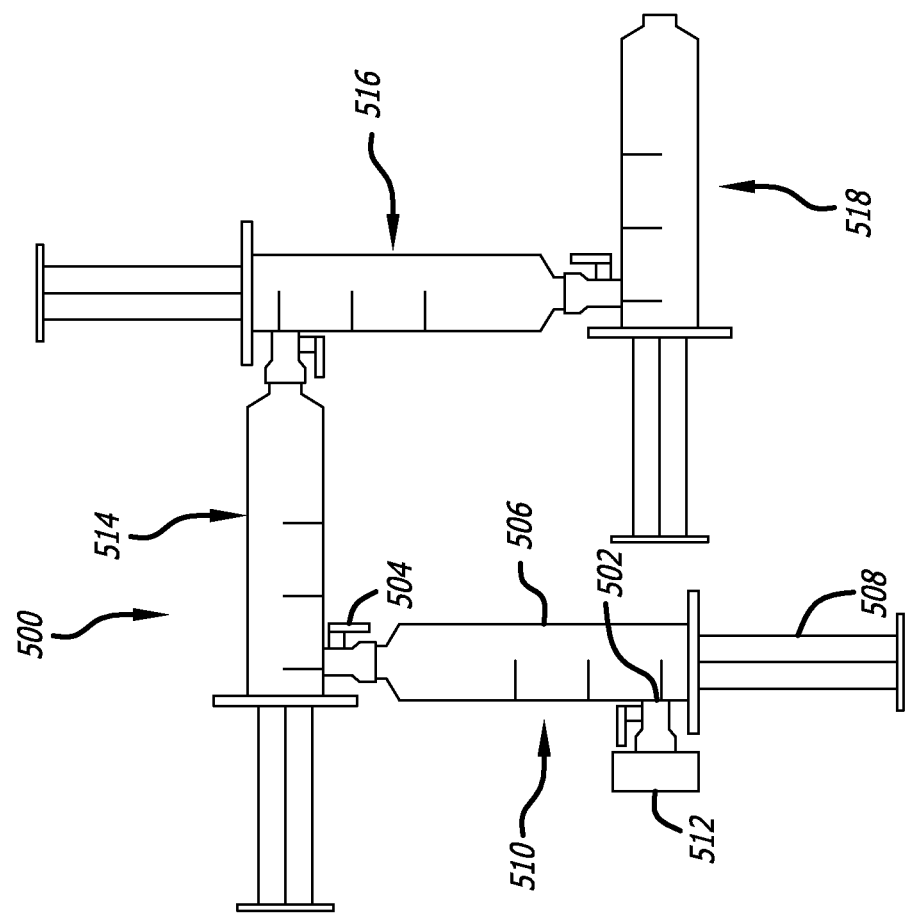

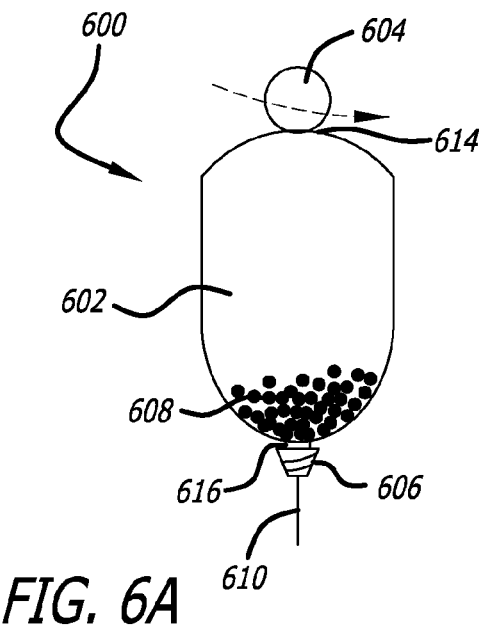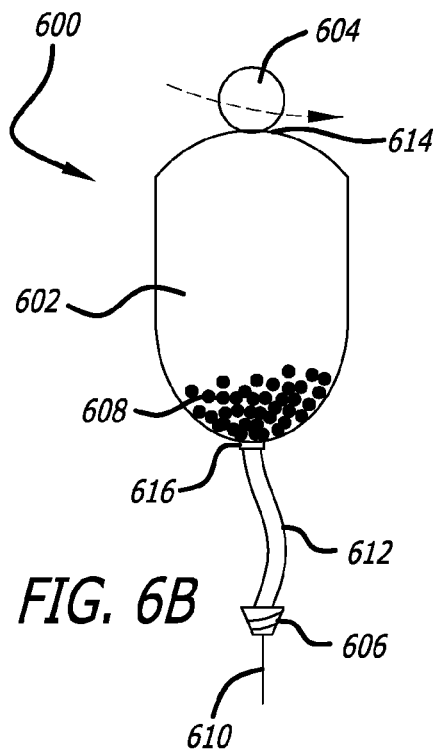
FIG. 6A    FIG. 6B
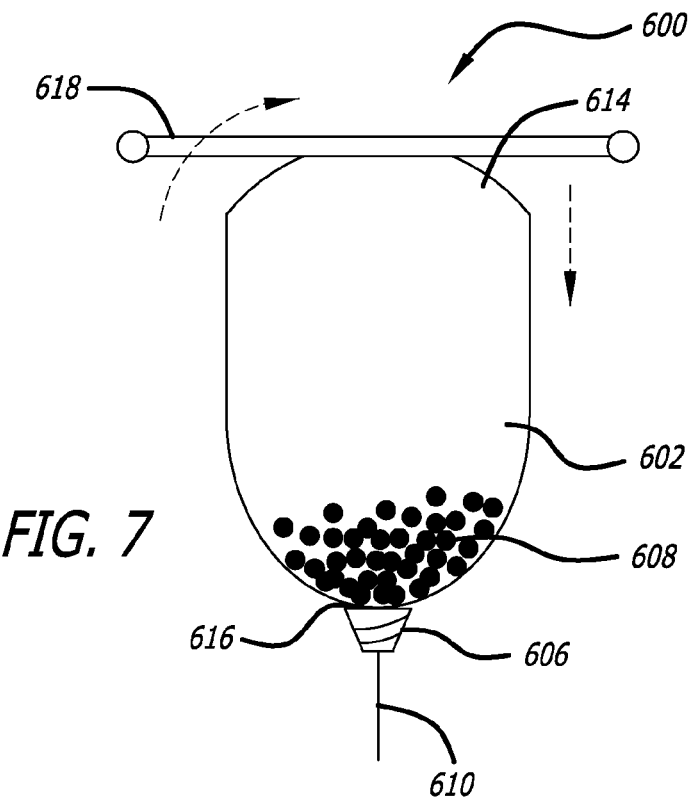
FIG. 7

ADIPOSE TISSUE COMBINATIONS, DEVICES, AND USES THEREOF

CROSS REFERENCE TO RELATED APPLICATIONS

This application claims the benefit of U.S. Provisional Patent Application Nos. 61/777,979, filed Mar. 12, 2013; 61/778,014, filed Mar. 12, 2013; 61/778,099, filed Mar. 12, 2013; 61/778,158, filed Mar. 12, 2013, and 61/778,210, filed Mar. 12, 2013, the entire disclosures of which are incorporated herein by reference.

FIELD

The present description generally relates to fat grafting procedures and more specifically relates to devices and methods for processing adipose tissue for re-introduction into the body.

BACKGROUND

Autologous fat transfer (AFT), also known as fat grafting, is a process by which fat is harvested from one part of a human body and injected into another part of the same person's body where additional bulk may be needed or desired for cosmetic and/or aesthetic purposes. Clinical applications for AFT are expanding rapidly. Autologous fat transfer has been reported for use in breast reconstruction and augmentation, buttock enhancement, treatment of congenital tissue defects, facial reconstruction, and skin rejuvenation. Although this is a very attractive approach and there is an increased trend in replacement of soft tissue volume with AFT, typical survival rates of grafted fat may be poor and overall results may not be satisfactory.

As such, there still remains a need for improved devices, systems, and methods for fat or adipose tissue grafting procedures.

SUMMARY

Systems for processing lipoaspirate, or aspirated adipose tissue, prior to reintroduction into the body are disclosed. The systems can introduce a combination or mixture of fat cells or adipose tissue and at least one additive into a target region of a patient. The system can provide parts for or be configured to actively mix the adipose tissue and additive(s).

In some embodiments, the systems can include containers for the collection and processing of fat or adipose tissue for re-injection into the body. In some embodiments, these containers can be flexible. In other embodiments, these flexible containers can be bags.

The containers can include two or more distinct compartments. For example, the containers can be compartmentalized containers including at least a first, a second and a third compartment and each compartment can be configured to perform or aid in a function of the systems described.

For example, in one embodiment, the first compartment can receive harvested lipoaspirate or adipose tissue. The first compartment may include a filter or other mechanism for initial adipose tissue processing. For example, the filter or other mechanism can be configured to separate adipose tissue from unwanted fluids and materials.

The second compartment, downstream of the first compartment, can be configured for receiving the processed adipose tissue. The second compartment may include one or more additives for mixing with the processed adipose tissue. The second compartment may include conduits for receiving additional harvested adipose tissue or the adipose tissue from the first compartment for enhancing mixing of these components and the additive(s).

The third compartment, downstream of the second compartment, may be configured to receive the adipose tissue/additive mixture and dispense it to a patient.

In some embodiments, systems for processing adipose tissue for reintroduction into the body can include: a container including at least a first compartment, a second compartment, and a third compartment, wherein the first compartment is configured to receive harvested adipose tissue, wherein the second compartment is connected to the first compartment and includes at least one additive, and wherein the third compartment is connected to the second compartment and is configured to dispense the adipose tissue and additive(s) to a patient.

In some embodiments, the systems further comprise an additional compartment including a tortuous path connecting the second compartment to the third compartment. The tortuous path can be configured to mix the additive and the adipose tissue.

In some embodiments, a frangible seal or a filter may separate the first compartment from the second compartment.

Also described herein are systems directed to manual or electromechanical injector devices that can mix adipose tissue with additives and then inject the mixture into a patient for tissue augmentation, breast augmentation or reconstruction, dermal filling or other tissue bulking purposes.

The manual or electromechanical injector devices can include: a first plunger configured to advance through a first chamber including adipose tissue; a second plunger configured to advance through a second chamber including at least one additive to a patient when mixed with the adipose tissue; a mixing chamber configured to receive and mix the adipose tissue and the at least one additive upon advancement of the first plunger and the second plunger; and a luer connector distal to the mixing chamber.

If electromechanical, the injector devices can include a drive mechanism configured to advance the first plunger and the second plunger. This drive mechanism can comprise a processor configured to control the a drive mechanism.

In some embodiments, a first drive mechanism is configured to advance the first plunger and a second drive mechanism is configured to advance the second plunger. In other embodiments, the mixing chamber includes a tortuous path.

In other embodiments, systems are described comprising a multi-purpose syringe for processing and mixing adipose tissue with at least one additive.

The multi-purpose syringe may include a first section and a second section which is divided into multiple containment sections. In some embodiments, the second section can be separable and connectable to the first section. The second section can include multiple, replaceable units wherein each replaceable unit includes features that perform a particular function of the fat grafting process.

A multi-purpose syringe may comprise: a first section including a barrel and a plunger having a plunger head, the plunger being slidable in the barrel; and multiple second sections, each being connectable and separable from the first section, and each second section performing a different fat grafting function.

In other embodiments fat grafting systems are described including a series of two or more syringes configured or arranged to provide a continuous flow of clean adipose tissue or a clean adipose tissue and additive mixture. The arrangement of two or more syringes with the provided flow can fill each syringe barrel, one at a time, for example, with only the last one in the series being partially full. The syringes can then be separated from each other, sealed off and used for injection.

Further still, systems are described for containing and dispensing harvested adipose tissue. The dispensing devices can be structured to contain, mix, dispense and implant freshly harvested and/or processed adipose tissue.

Such systems can include: a pliable container having a proximal end and a distal end and an internal volume configured to contain harvested adipose tissue; a mechanism, configured to manipulate the pliable container to force the harvested adipose tissue toward the distal end; and a dispensing element, disposed at the distal end, configured to enable dispensing of the harvested adipose tissue.

In some embodiments, an additive can be located in the pliable container. The additive may be suitable for combining with harvested adipose tissue. The pliable container can be configured to manually mix the harvested adipose tissue and the additive.

The systems can further include a luer connector disposed at the dispensing element.

In some embodiments, the systems can include a mechanism comprising a twistable ring configured to reduce the internal volume of the pliable container. In other embodiments, the systems can include a mechanism comprising a moveable bar configured to reduce the internal volume of the pliable container.

BRIEF DESCRIPTION OF THE DRAWINGS

The present description may be more clearly understood and the advantages thereof better appreciated by considering the below Detailed Description and accompanying Drawings of which:

FIG. 2 illustrates exemplary internal components of an electromechanical injection device as described.

FIG. 5A illustrates a series of syringes set for filling. FIG. 5B illustrates a dual barrel syringe.

FIGS. 6A and 6B illustrate a simplified view of dispensing devices with a needle and cannula respectively.

FIG. 7 illustrates a simplified view of another dispensing device including a twist bar.

DETAILED DESCRIPTION

Figure 1:
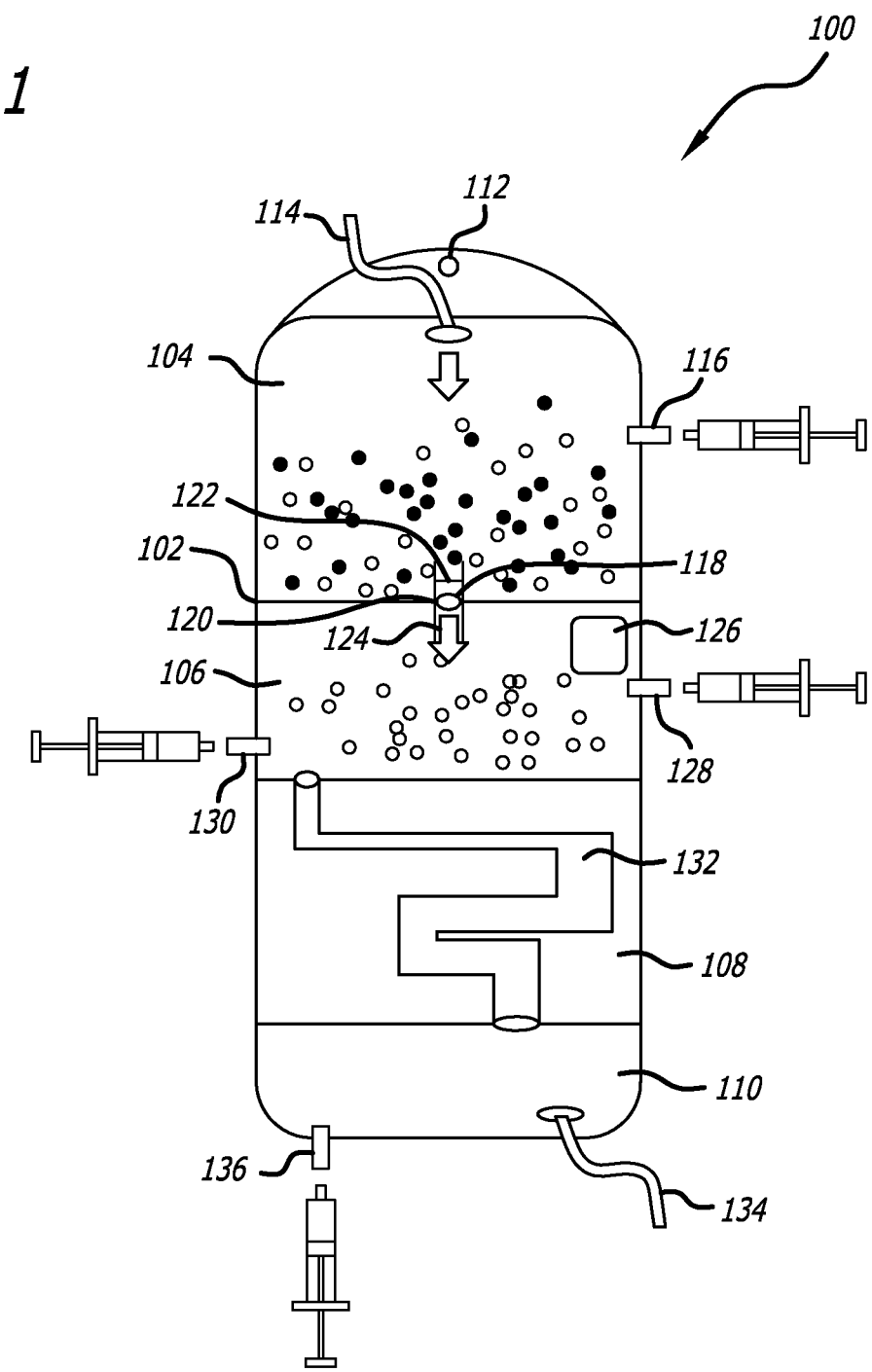
FIG. 1 illustrates an example view of a system as described herein.

The systems described are generally configured to mix harvested adipose tissue with one or more additives. In one embodiment the adipose tissue may be freshly harvested. The mixing of adipose tissue with one or more additives can be for improved viability of the adipose tissue when implanted back into a patient, for example, for breast augmentation, body contouring, dermal filling, reconstructive purposes, or the like.

As used herein, fat cells include the terms "adipose tissue," "fat," "fat tissue", or "fatty tissue" which include loose fibrous connective tissue comprising adipocytes and multiple types of regenerative cells, and may comprise brown and/or white adipose tissue taken from any body site, such as, e.g., subcutaneous, omental/visceral, interscapular, or mediastinal. It may be obtained from any organism having adipose tissue, or the adipose tissue used may be from a primary cell culture or an immortalized cell line.

Adipose tissue may be collected from the same individual who is undergoing the soft tissue replacement procedure (autograft), from a donor individual who is not the same individual as the one undergoing the soft tissue replacement procedure (allograft), or from an animal source (xenograft). As used herein, the term "autotransplantation" includes the transplantation of organs, tissues, or cells from one part of the body to another part in the same individual, i.e., the donor and recipient are the same individual. Tissue transplanted by such "autologous" procedures can be referred to as an autograft or autotransplant. As used herein, the term "allotransplantation" includes the transplantation of organs, tissues, or cells from a donor to a recipient, where the donor and recipient are different individuals, but of the same species. Tissue transplanted by such "allologous" procedures can be referred to as an allograft or allotransplant. As used herein, the term "xenotransplantation" includes the transplantation of organs, tissues, or cells from a donor to a recipient, where the donor is of a different species than the recipient. Tissue transplanted by such "xenologous" procedures can be referred to as a xenograft or xenotransplant.

Adipose tissue can be collected by any procedure that can harvest adipose tissue useful for the compositions and methods disclosed herein, including, without limitation a liposuction (lipoplasty) procedure or a lipectomy procedure. Procedures useful for collecting adipose tissue should minimize the trauma and manipulation associated with adipose tissue removed. Adipose tissue may be harvested from any suitable region, including, without limitation, a mammary region, an abdominal region, a thigh region, a flank region, a gluteal region, a trochanter region, or a gonadal region. Procedures useful for collecting adipose tissue are well known to a person of ordinary skill in the art. The selected procedures may be performed concomitantly with liposculpture.

A liposuction procedure harvests adipose tissue by aspirating the tissue using a cannula. The cannula may be connected to a syringe for manual aspiration or to a power assisted suction device, like an aspirator, adapted to collect the adipose tissue into a vacuum bottle. A liposuction procedure does not maintain an intact blood supply of the harvested tissue. The syringe may be a 10, 20 or 60 mL syringe fitted with a 12 or 14 gauge cannula. Non-limiting examples of liposuction procedures include suction-assisted liposuction (SAL), ultrasound-assisted liposuction (UAL), power-assisted liposuction (PAL), twin-cannula (assisted) liposuction (TCAL or TCL), or external ultrasound-assisted liposuction (XUAL or EUAL), or water-assisted liposuction (WAL). In addition, the liposuction procedures listed above can be used with any of the following procedures that vary the amount of fluid injected during the procedure, such as, e.g., dry liposuction, wet liposuction, super-wet liposuction, tumescent liposuction, or laser-assisted liposuction. An autologous soft tissue transfer procedure typically uses adipose tissue collected from a liposuction procedure.

Although the harvested tissue may be used directly to make the disclosed compositions, it is more typically processed to purify and/or enrich for healthy adipocytes and regenerative cells. For example, the harvested adipose tissue may be separated from any debris and/or contaminants such as, e.g., blood, serum, proteases, lipases, lipids and other oils, and/or other bodily fluids; tumescent fluid and/or other materials used in the liposuction procedure; and/or other impurities suctioned during the procedure. Methods useful in separating debris and/or contaminants from adipose tissue to make the disclosed compositions include, without limitation, centrifugation, sedimentation, filtration, and/or absorption. In addition, or alternatively, the harvested adipose tissue may be processed by washing it in a physiological buffer like saline to remove any debris and/or contaminants.

A lipectomy procedure harvests adipose tissue by surgical excision from a donor site in a manner that minimizes damage to the blood supply of the tissue using standard surgical operative procedures. This harvested tissue is then implanted into the region needing the soft tissue replacement. A tissue flap or tissue graft procedure typically uses adipose tissue collected from a lipectomy procedure. A tissue flap is a section of living tissue that maintained its blood supply as the tissue is moved from one area of the body to another.

A local flap uses a piece of skin and underlying tissue that lie adjacent to the wound, including adipose tissue. The flap remains attached at one end so that it continues to be nourished by its original blood supply, and is repositioned over the wounded area. A regional flap uses a section of tissue that is attached by a specific blood vessel. When the flap is lifted, it needs only a very narrow attachment to the original site to receive its nourishing blood supply from the tethered artery and vein. A musculocutaneous flap, also called a muscle and skin flap, is used when the area to be covered needs more bulk and a more robust blood supply. Musculocutaneous flaps are often used in breast reconstruction to rebuild a breast after mastectomy. As an example, the transverse rectus abdominus myocutaneous) flap (TRAM flap) is a tissue flap procedure that uses muscle, fat and skin from an abdomen to create a new breast mound after a mastectomy. This type of flap remains "tethered" to its original blood supply. In a bone/soft tissue flap, bone, along with the overlying skin, is transferred to the wounded area, carrying its own blood supply.

Typically, a wound that is wide and difficult or impossible to close directly may be treated with a skin graft. A skin graft is a patch of healthy skin that is taken from one area of the body, called the "donor site," and used to cover another area where skin is missing or damaged. There are three basic types of skin grafts. A split-thickness skin graft, commonly used to treat burn wounds, uses only the layers of skin closest to the surface. A full-thickness skin graft might be used to treat a burn wound that is deep and large, or to cover jointed areas where maximum skin elasticity and movement are desired. As its name implies, a full-thickness (all layers) section of skin from the donor site are lifted. A composite graft is used when the wound to be covered needs more underlying support, as with skin cancer on the nose. A composite graft requires lifting all the layers of skin, adipose tissue, and sometimes the underlying cartilage from the donor site.

The amount of adipose tissue collected will typically vary from individual to individual and can depend on a number of factors including, but not limited to, amount of adipose tissue required for the soft tissue replacement method, aesthetic expectations, age, body habitus, coagulation profile, hemodynamic stability, co-morbidities, and physician preference. A liposuction procedure may harvest from about 1 mL to about 1500 mL of adipose tissue. A lipectomy procedure typically harvests about 1 g to about 5,000 g.

Adipose tissue comprises multiple types of regenerative cells. As used herein, the term "regenerative cell" refers to any cells that cause or contribute to complete or partial regeneration, restoration, or substitution of structure or function of an organ, tissue, or physiologic unit or system to thereby provide a therapeutic, structural or cosmetic benefit. Examples of regenerative cells include stem cells, progenitor cells, and precursor cells.

As used herein, the term "stem cell" refers to a multipotent regenerative cell with the potential to differentiate into a variety of other cell types that perform one or more specific functions and has the ability to self-renew. Some of the stem cells disclosed herein may be pluripotent. Exemplary examples of stem cells include, without limitation, adipose-derived stem cells (ASCs; adipose-derived stromal cells), endothelial-derived stem cells (ESCs), hemopoietic stem cells (HSCs), and mesenchyma stem cells (MSCs). Examples of differentiation include angiogenesis, neovascularization, adipogenesis and collagenesis.

As used herein, the term "progenitor cell" includes an oligopotent regenerative cell with the potential to differentiate into more than one cell type, or a unipotent regenerative cell with the potential to differentiate into only a single cell type, that perform(s) one or more specific functions and has limited or no ability to self-renew. Exemplary examples of progenitor cells include, without limitation, endothelial progenitor cells, keratinocytes, monoblasts, myoblasts, and pericytes.

As used herein, the term "precursor cell" includes a unipotent regenerative cell with the potential to differentiate into one cell type that performs one or more specific functions and may retain extensive proliferative capacity that enables the cells to proliferate under appropriate conditions. Exemplary examples of precursor cells include, without limitation, adipoblast (lipoblast or preadipocytes), de-differentiated adipocytes, angioblasts, endothelial precursor cells, fibroblasts, lymphoblasts, and macrophages.

A hydrogel composition disclosed herein may enhance differentiation of the multiple regenerative cells from the adipose tissue. In one embodiment, a hydrogel composition disclosed herein enhances differentiation of the multiple regenerative cells from the adipose tissue as compared to adipose tissue alone. In aspects of this embodiment, a hydrogel composition disclosed herein enhances differentiation of the multiple regenerative cells from the adipose tissue by at least about 50%, at least about 100%, at least about 150%, at least about 200%, at least about 250%, at least about 300%, at least about 350%, at least about 400%, at least about 450%, at least about 500%, at least about 750%, or at least about 1000% as compared to adipose tissue alone. In aspects of this embodiment, a hydrogel composition disclosed herein enhances differentiation of the multiple regenerative cells from the adipose tissue by about 50% to about 250%, about 50% to about 500%, about 50% to about 1000%, about 100% to about 300%, about 100% to about 500%, about 100% to about 1000%, about 150% to about 400%, about 150% to about 600%, about 150% to about 1000%, about 200% to about 500%, about 200% to about 700%, or about 200% to about 1000% as compared to adipose tissue alone.

In another embodiment, a hydrogel composition disclosed herein enhances differentiation of the multiple regenerative cells from the adipose tissue as compared to adipose tissue with a hydrogel composition that is substantially identical except that the hyaluronic acid component and the collagen component are not crosslinked. In aspects of this embodiment, a hydrogel composition disclosed herein enhances differentiation of the multiple regenerative cells from the adipose tissue by at least about 50%, at least about 100%, at least about 150%, at least about 200%, at least about 250%, at least about 300%, at least about 350%, at least about 400%, at least about 450%, at least about 500%, at least about 750%, or at least about 1000% as compared to adipose tissue with a hydrogel composition that is substantially identical except that the hyaluronic acid component and the collagen component are not crosslinked. In aspects of this embodiment, a hydrogel composition disclosed herein enhances differentiation of the multiple regenerative cells from the adipose tissue by about 50% to about 250%, about 50% to about 500%, about 50% to about 1000%, about 100% to about 300%, about 100% to about 500%, about 100% to about 1000%, about 150% to about 400%, about 150% to about 600%, about 150% to about 1000%, about 200% to about 500%, about 200% to about 700%, or about 200% to about 1000% as compared to adipose tissue with a hydrogel composition that is substantially identical except that the hyaluronic acid component and the collagen component are not crosslinked. In another aspect of this embodiment, a hydrogel composition that is substantially identical to a hydrogel composition disclosed herein except that the hyaluronic acid component and the collagen component are not crosslinked comprises hyaluronic acid at a concentration of about 16 mg/mL or about 24 mg/mL and water.

In yet another embodiment, a hydrogel composition disclosed herein enhances differentiation of the multiple regenerative cells from the adipose tissue as compared to adipose tissue with a hydrogel composition that is substantially identical except that the collagen component is absent. In aspects of this embodiment, a hydrogel composition disclosed herein enhances differentiation of the multiple regenerative cells from the adipose tissue by at least about 50%, at least about 100%, at least about 150%, at least about 200%, at least about 250%, at least about 300%, at least about 350%, at least about 400%, at least about 450%, at least about 500%, at least about 750%, or at least about 1000% as compared to adipose tissue with a hydrogel composition that is substantially identical except that the collagen component is absent. In aspects of this embodiment, a hydrogel composition disclosed herein enhances differentiation of the multiple regenerative cells from the adipose tissue by about 50% to about 250%, about 50% to about 500%, about 50% to about 1000%, about 100% to about 300%, about 100% to about 500%, about 100% to about 1000%, about 150% to about 400%, about 150% to about 600%, about 150% to about 1000%, about 200% to about 500%, about 200% to about 700%, or about 200% to about 1000% as compared to adipose tissue with a hydrogel composition that is substantially identical except that the collagen component is absent. In another aspect of this embodiment, a hydrogel composition that is substantially identical to a hydrogel composition disclosed herein except that the collagen component is absent, comprises hyaluronic acid at a concentration of about 16 mg/mL or about 24 mg/mL and water.

Harvested adipose tissue useful in compositions of the systems can be supplemented with regenerative cells such as, e.g., stem cells, progenitor cells, and precursor cells. Regenerative cells may promote new blood vessel formation, diminish necrosis, and/or promote a supportive microenvironment in the transplanted tissue, thereby improving survivability of the transplanted tissue. Regenerative cells can be obtained from a variety of sources. For example, adipose tissue is rich in regenerative cells that have the ability to restore and reconstruct various soft tissue defects in response to local differentiation clues from the recipient site. As such, a portion of the collected adipose tissue may be further processed in order to purify regenerative cells that can then be added back to the remainder of the harvested adipose tissue in order to enrich this material for these cells. Exemplary methods describing such cell enrichment procedures can be found in, e.g., Hedrick and Fraser, Methods of Using Adipose Tissue-Derived Cells in Augmenting Autologous Fat Transfer, U.S. Patent Publication 2005/0025755, Yoshimura, et al., Characterization of Freshly Isolated and Cultured Cells Derived form the Fatty and Fluid Portions of liposuction Aspirates, J. Cell. Physiol. 208: 1011-1041 (2006); Yoshimura, et al., Cell-Assisted Lipotransfer for Facial Lipoatrophy: Effects of Clinical Use of Adipose-Derived Stem Cells, Dermatol. Surg. 34: 1178-1185 (2008); Yoshimura, et al., Cell-Assisted Lipotransfer for Cosmetic Breast Augmentation: Supportive Use of Adipose-Derived Stem/Stromal Cells, Aesth. Plast. Surg. 32: 48-55 (2008); each of which is hereby incorporated by reference in its entirety.

In addition, harvested adipose tissue can be supplemented with regenerative cells obtained from cell cultures, such as, e.g., primary cell cultures and established cell cultures. For example, a portion of harvested adipose tissue from an individual can be cultured in a manner to produce primary cell cultures enriched for regenerative cells. Alternatively, established cell lines derived from regenerative cells from adipose tissue, or another tissue source, can be cultured, harvested, and added to adipose tissue collected from an individual. Exemplary methods describing such cell culture compositions and procedures can be found in, e.g., Casteilla, et al., Method for Culturing Cells Derived from the Adipose Tissue and Uses Thereof, U.S. Patent Publication 2009/0246182; Chazenbalk, et al, Methods of Producing Preadipocytes and Increasing the Proliferation of Adult Adipose Stem/Progenitor Cells, U.S. Patent Publication 2009/0317367; Kleinsek and Soto, Augmentation and Repair of Sphincter Defects with Cells Including Adipocytic Cells, U.S. Patent Publication 2008/0299213; Rehman, et al., Secretion of Angiogenic and Antiapoptotic Factors by Human Adipose Stromal Cells, Circulation 109: r52-r58 (2004); Kilroy, et al., Cytokine Profile of Human Adipose-Derived Stem Cells: Expression of Angiogenic, Hematopoietic, and Pro-Inflammatory Factors, J. Cell. Physiol. 212: 702-709 (2007); each of which is hereby incorporated by reference in its entirety.

Harvested adipose tissue may be immediately used to make the compositions disclosed herein. Alternatively, harvested adipose tissue, whether unprocessed or processed, may be stored for used at some future date. Harvested tissue is typically stored using a slow freezing method of the tissue to −20° C., with or without cryopreservatives. Stored adipose tissue can typically be stored for at least 6 months.

Additives can be any material that may be mixed with cellular material, for example, living cells, for example, fat cells or adipose tissue, and which can maintain the viability of the cellular material when mixed therewith and then injected or implanted in a body. Such additives may be in the form of hydrogels that enhance, promote or support cell proliferation or survival. Additives can be hyaluronic acid based additives. In other embodiments, the additive can be a hydrogel composition. The hydrogel composition may comprise a hyaluronic acid component and a collagen component, for example, a hyaluronic acid component crosslinked to a collagen component.

Further additives useful in the present devices are described, for example, in commonly owned U.S. patent application Ser. No. 13/740,712, filed on Jan. 14, 2013, the entire disclosure of which is incorporated herein by this reference.

Hydrogels described herein may also be used to enhance, promote or support cell proliferation or survival. Some embodiments include a method comprising contacting or mixing a hydrogel or a hydrogel composition with a adipose tissue.

A hydrogel or a hydrogel composition that contacts one or more adipose tissue may promote or support survival of the fat cells. For example, a hydrogel or a hydrogel composition described herein may promote or support fat cell survival to a greater extent than a hydrogel composition comprising hyaluronic acid having a weight concentration that is similar to the weight concentration of the crosslinked macromolecular matrix used in a hydrogel described herein. In some embodiments, a hydrogel or a hydrogel composition described herein may promote or support fat cell survival to a greater extent than a hydrogel composition comprising water and hyaluronic acid at a concentration of about 24 mg/mL or about 16 mg/mL. Contact or mixture of a hydrogel or a hydrogel composition described herein and fat cells may promote or support cell survival in vivo to a greater extent than a hydrogel composition that is substantially identical except that the hyaluronic acid component and the collagen component are not crosslinked. In some embodiments, a hydrogel or a hydrogel composition may promote or support fat cell survival about as well as, or better than, tissue culture polystyrene.

In some methods, hydrogel or a hydrogel composition may be mixed with adipose tissue or fat tissue or fat cells from a human being, such as human lipoaspirate, or from fat from another human being or an animal. The ratio of hydrogel to fat cells in such a mixture may vary to provide the desired results. The fat cell:hydrogel ratio is the weight of the fat cells divided by the weight of hydrogel. For example, if 1 gram of fat cells is mixed with 10 grams of hydrogel, the fat cell:hydrogel weight ratio is 0.1. In some embodiments, the fat cells and the hydrogel may have a fat cell:hydrogel weight ratio of about 0.1 up to about 10. All other fat cell:hydrogel weight ratios falling within this range are also contemplated and considered to be within the scope of the present disclosure. For example, the weight ratio may be about 0.5 up to about 7, for example, about 1 up to about 5. In some embodiments, the fat cell:hydrogel weight ratio is about 1 to about 3, for example, about 1, about 2, or about 3.

A combination or mixture of human adipose tissue and hydrogel composition may then be injected or implanted into soft tissue of a human being, for augmenting a body part or region such as a breast. This may help to improve the survival time of grafted fat cells in autologous and other fat transfer procedures. It may also help to improve volume retention, reduce the variability in retained fat graft volume, and/or reduce inflammation as compared to injecting fat cells alone.

A hydrogel and fat cell composition disclosed herein may show improved volume retention after injection or implantation into a soft tissue. In an embodiment, a hydrogel composition disclosed herein shows improved volume retention after injection or implantation into a soft tissue as compared to a hydrogel composition that is substantially identical except that the hyaluronic acid component and the collagen component are not crosslinked. In aspects of this embodiment, a hydrogel composition disclosed herein may show improved volume retention after injection or implantation into a soft tissue by at least about 5%, at least about 10%, at least about 15%, at least about 20%, at least about 25%, at least about 30%, at least about 35%, at least about 40%, at least about 45%, or at least about 50% as compared to a hydrogel composition that is substantially identical except that the hyaluronic acid component and the collagen component are not crosslinked. In aspects of this embodiment, a hydrogel composition disclosed herein shows improved volume retention after injection or implantation into a soft tissue by about 5% to about 25%, about 5% to about 50%, about 10% to about 30%, about 10% to about 50%, about 15% to about 40%, about 15% to about 50%, or about 20% to about 50% as compared to a hydrogel composition that is substantially identical except that the hyaluronic acid component and the collagen component are not crosslinked. In another aspect of this embodiment, a hydrogel composition that is substantially identical to a hydrogel composition disclosed herein, except that the hyaluronic acid component and the collagen component are not crosslinked, comprises hyaluronic acid at a concentration of about 16 mg/mL or about 24 mg/mL and water.

A hydrogel or a hydrogel composition may have improved physical properties that may help to encourage fat cell survival or proliferation in the mixture once implanted. In some embodiments, a hydrogel or a hydrogel composition may allow diffusion of adipose tissue-specific growth factors or pro-angiogenic growth factors to a greater extent than a hydrogel composition comprising hyaluronic acid at a concentration of about 24 mg/mL or about 16 mg/mL and water.

A filler comprising a hydrogel and fat cell mixture may be suitable for injection if it can be injected into the soft tissue of interest without unreasonable difficulty, and includes filler compositions that can be dispensed from syringes having a gauge as low as about #30 or about #25 under normal manual pressure with a smooth extrusion plateau.

Injection of a hydrogel and fat cell mixture may provide a soft tissue augmentation that mimics the natural components of the skin. A hydrogel and fat cell mixture may be injected intradermally or subcutaneously to augment soft tissue and to repair or correct congenital anomalies, acquired defects, or cosmetic defects. Examples of such conditions include congenital anomalies such as hemifacial microsomia, malar and zygomatic hypoplasia, unilateral mammary hypoplasia, pectus excavatum, pectoralis agenesis (Poland's anomaly), and velopharyngeal incompetence secondary to cleft palate repair or submucous cleft palate (as a retropharyngeal implant); acquired defects (post traumatic, post surgical, or post infectious) such as depressed scars, subcutaneous atrophy (e.g., secondary to discoid lupis erythematosis), keratotic lesions, enopthalmos in the unucleated eye (also superior sulcus syndrome), acne pitting of the face, linear scleroderma with subcutaneous atrophy, saddle-nose deformity, Romberg's disease, and unilateral vocal cord paralysis; and cosmetic defects such as glabellar frown lines, deep nasolabial creases, circum-oral geographical wrinkles, sunken cheeks, and mammary hypoplasia.

A hydrogel may comprise water and a crosslinked macromolecular matrix. Typically, a crosslinked molecular matrix may comprise a hyaluronic acid component and a collagen component, wherein the hyaluronic acid component is crosslinked to the collagen component by a crosslinking component. A crosslinking component may comprise a plurality of crosslink units, wherein at least a portion of the crosslink units comprise an ester bond or an amide bond. Fat cells may be mixed with such networks.

A hydrogel or a hydrogel composition may be at least about 70%, about 93%, or about 96% water by weight, and may approach 100% water by weight. A crosslinked macromolecular matrix may be about 0.01% to about 30%, about 0.1% to about 7%, or about 0.2% to about 4% of the weight of a hydrogel or a hydrogel composition. A hyaluronic acid component may be about 0.005% to about 20%, about 0.1% to about 5% or about 0.2% to about 2.5% of the total weight of a hydrogel or a hydrogel composition. A collagen component may be about 0.01% to about 10%, about 0.03% to about 2%, or about 0.05% to about 1.2% of the total weight of a hydrogel or a hydrogel composition.

A crosslinked macromolecular matrix for a hydrogel may be synthesized by coupling a hyaluronic acid with a collagen using a coupling agent, such as a carbodiimide. In these hydrogels, hyaluronic acid may serve as a biocompatible water-binding component, providing bulk and isovolumetric degradation. Additionally, collagen may impart cell adhesion and signaling domains to promote cell attachment, migration, and other cell functions such as extra-cellular matrix deposition. The biopolymers form homogeneous hydrogels with tunable composition, swelling, and mechanical properties. Compositions can be made to be injectable for minimally invasive implantation through syringe and needle.

Hyaluronic acid is a non-sulfated glycosaminoglycan that enhances water retention and resists hydrostatic stresses. It is non-immunogenic and can be chemically modified in numerous fashions. Hyaluronic acid may be anionic at pH ranges around or above the pKa of its carboxylic acid groups. Unless clearly indicated otherwise, reference to hyaluronic acid herein may include its fully protonated, or nonionic form as depicted below, as well as any anionic forms and salts of hyaluronic acid, such as sodium salts, potassium salts, lithium salts, magnesium salts, calcium salts, etc.

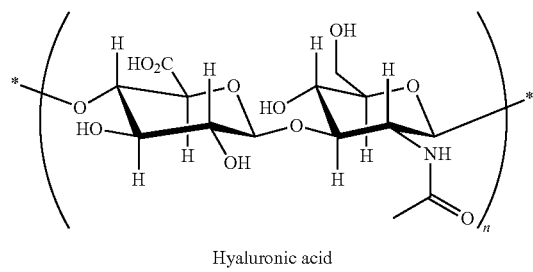

Hyaluronic acid

Collagen is a protein that forms fibrils and sheets that bear tensile loads. Collagen also has specific integrin-binding sites for cell adhesion and is known to promote cell attachment, migration, and proliferation. Collagen may be positively charged because of its high content of basic amino acid residues such as arginine, lysine, and hydroxylysine. Unless clearly indicated otherwise, reference to collagen herein may include uncharged collagen, as well as any cationic forms, anionic forms, or salts of collagen.

Because hyaluronic acid may be anionic and collagen may be cationic, the two macromolecules may form polyionic complexes in aqueous solution. A polyionic complex may be significantly less soluble in water than either hyaluronic acid or collagen, and thus may precipitate out of aqueous solution when the two macromolecules are together in a mixture. Furthermore, collagens are often soluble only at low pH and may precipitate from solution when brought to a pH amenable to carbodiimide coupling.

Under some conditions, a hyaluronic acid and a collagen may be combined in an aqueous liquid in which both components are soluble. A hyaluronic acid and a collagen may then be crosslinked while both are dissolved in an aqueous solution to form a hydrogel. Reaction conditions such as the concentration of hyaluronic acid, the concentration of collagen, the pH of the solution, and salt concentration may be adjusted to help to prevent polyionic complex formation between anionic hyaluronic acid and cationic collagen. They may also help to prevent collagen microfibril formation, which results in precipitation from solution and may prevent crosslinking. Fat cells may be mixed with this polyionic complex.

Some embodiments include hydrogels which can be mixed with adipose tissue, wherein the hydrogels are formed by a method of crosslinking hyaluronic acid and collagen. This method generally comprises a dissolution step which results in an aqueous pre-reaction solution. In a dissolution step, hyaluronic acid and collagen are dissolved in an aqueous solution that has a low pH and/or a salt to form an aqueous pre-reaction solution.

A hyaluronic acid-collagen crosslinking method further comprises an activation step. In an activation step, an aqueous pre-reaction solution is modified by at least adding a water soluble coupling agent and/or by increasing the pH of the solution. If needed, a salt may also be added to keep the hyaluronic acid and collagen in solution at the higher pH. Thus, a crosslinking reaction mixture comprises hyaluronic acid and collagen dissolved or dispersed in an aqueous medium, a water soluble coupling agent, and a salt, and has a higher pH than the aqueous pre-reaction solution from which it was derived. The crosslinking reaction mixture is allowed to react to thereby crosslink the hyaluronic acid and the collagen.

In some embodiments, the pH of the aqueous pre-reaction solution may be increased and a substantial amount of fiber formation may be allowed to occur in the solution before adding the water soluble coupling agent. In some embodiments, the water soluble coupling agent may be added to the aqueous pre-reaction solution before substantially any fiber formation occurs.

A crosslinking reaction mixture can react to form a crosslinked macromolecular matrix. Since reaction occurs in an aqueous solution, a crosslinked macromolecular matrix may be dispersed in an aqueous liquid in hydrogel form as it is formed by a crosslinking reaction. A crosslinked macromolecular matrix may be kept in hydrogel form because, in many instances, a crosslinked macromolecular matrix may be used in hydrogel form.

In some embodiments, an aqueous pre-reaction solution or a crosslinking reaction mixture may further comprise about 10% to about 90% of an organic solvent in which hyaluronic acid has poor solubility, such as ethanol, methanol, isopropanol, or the like.

After a crosslinking reaction has occurred, the crosslinked macromolecular matrix may be particulated or homogenized through a mesh. This may help to form an injectable slurry or hydrogel. A mesh used for particulating a crosslinked macromolecular matrix may have any suitable pore size depending upon the size of particles desired. In some embodiments, the mesh may have a pore size of about 10 microns to about 100 microns, about 50 microns to about 70 microns, or about 60 microns.

A hydrogel comprising a crosslinked molecular matrix may be treated by dialysis for sterilization or other purposes. Dialysis may be carried out by placing a semipermeable membrane between the hydrogel and another liquid so as to allow the hydrogel and the liquid to exchange molecules or salts that can pass through the membrane.

A dialysis membrane may have a molecular weight cutoff that may vary. For example, the cutoff may be about 5,000 Daltons to about 100,000 Daltons, about 10,000 Daltons to about 30,000 Daltons, or about 20,000 Daltons.

The dialysis may be carried out against a buffer solution, meaning that the liquid on the other side of the membrane from the hydrogel may be a buffer solution. In some embodiments, the buffer solution may be a sterile phosphate buffer solution that may comprise phosphate buffer, potassium chloride, and/or sodium chloride. A sterile phosphate buffer solution may be substantially isosmotic with respect to human physiological fluid. Thus, when dialysis is complete, the liquid component of a hydrogel may be substantially isosmotic with respect to human physiological fluid. This hydrogel can then be mixed with additives such as adipose tissue as described herein using a device as described herein.

In some embodiments, a crosslinked macromolecular complex may further comprise an aqueous liquid. For example, the crosslinked macromolecular complex may absorb the aqueous liquid so that a hydrogel is formed. An aqueous liquid may comprise water with a salt dissolved in it, such as a phosphate buffer, sodium chloride, potassium chloride, etc. In some embodiments, an aqueous liquid may comprise water, sodium chloride at a concentration of about 100 mM to about 200 mM, potassium chloride at a concentration of about 2 mM to about 3 mM, and a phosphate buffer at a concentration of about 5 mM to about 15 mM, wherein the pH of the liquid is about 7 to about 8.

In some embodiments, an anesthetic may be included in any composition comprising a crosslinked macromolecular complex or other hydrogel described herein before being mixed with an additive such as adipose tissue. The anesthetic can be present in an amount effective to mitigate pain experienced upon injection of the composition. Examples of an anesthetic may include, but are not limited to, ambucaine, amolanone, amylocalne, benoxinate, benzocaine, betoxycaine, biphenamine, bupivacaine, butacaine, butamben, butanilicaine, butethamine, butoxycaine, carticaine, chloroprocaine, cocaethylene, cocaine, cyclomethycaine, dibucaine, dimethysoquin, dimethocaine, diperodon, dycyclonine, ecgonidine, ecgonine, ethyl chloride, etidocaine, beta-eucaine, euprocin, fenalcomine, formocaine, hexylcaine, hydroxytetracaine, isobutyl p-aminobenzoate, leucinocaine mesylate, levoxadrol, lidocaine, mepivacaine, meprylcaine, metabutoxycaine, methyl chloride, myrtecaine, naepaine, octacaine, orthocaine, oxethazaine, parethoxycaine, phenacaine, phenol, piperocaine, piridocaine, polidocanol, pramoxine, prilocaine, procaine, propanocaine, proparacaine, propipocaine, propoxycaine, psuedococaine, pyrrocaine, ropivacaine, salicyl alcohol, tetracaine, tolycaine, trimecaine, zolamine, and salts thereof. In some embodiments, the at least one anesthetic agent is lidocaine, such as in the form of lidocaine HCl. The concentration of lidocaine may vary. For example, some compositions may have about 0.1% to about 5%, about 0.2% to about 1.0%, or about 0.3% lidocaine by weight (w/w %) of the composition. The lidocaine concentration in the compositions described herein can be therapeutically effective meaning the concentration may be adequate to provide a therapeutic benefit without inflicting harm.

A hydrogel mixed with an additive may be used in a soft tissue aesthetic product. An aesthetic product includes any product that improves any aesthetic property of any part of an animal or human being. A soft tissue aesthetic product may comprise: an aesthetic device having a form suitable for injecting or implanting into a tissue; and a label comprising instructions to inject or implant the aesthetic component into a tissue; wherein the aesthetic device comprises a crosslinked macromolecular matrix described herein. Some products may comprise the crosslinked macromolecular matrix in hydrogel form.

Some embodiments include a method of improving an aesthetic quality of an anatomic feature of a human being. Improving an aesthetic quality of an anatomic feature of a human being includes improving any kind of aesthetic quality including appearance, tactile sensation, etc., and improving any anatomical feature, including those of the face, limbs, breasts, buttocks, hands, etc. Such a method may comprise injecting or implanting an aesthetic device into a tissue of the human being to thereby improve the aesthetic quality of the anatomic feature; wherein the aesthetic device comprises a crosslinked macromolecular matrix composition described herein. In some embodiments, the crosslinked macromolecular matrix used in the product may be in hydrogel form.

In some embodiments, a hydrogel of a crosslinked macromolecular complex may have a storage modulus of about 1 Pa to about 10,000 Pa, about 50 Pa to about 10,000 Pa, about 50 Pa to about 6000 Pa, about 80 Pa to about 2000 Pa, about 500 Pa to about 1000 Pa, about 500 Pa to about 4000 Pa, about 500 Pa to about 5000 Pa, about 556 Pa, about 560 Pa, about 850 Pa, about 852 Pa, about 1000 Pa, or any value in a range bounded by, or between, any of these values.

In some embodiments, a hydrogel of a crosslinked macromolecular complex may have a loss modulus of about 1 Pa to about 500 Pa, about 10 Pa to 200 Pa, about 100 Pa to about 200 Pa, about 20 Pa, about 131 Pa, about 152 Pa, or any value in a range bounded by, or between, any of these values.

In some embodiments, a hydrogel of a crosslinked macromolecular complex may have an average extrusion force of about 10 N to about 50 N, about 20 N to 30 N, or about 25 N, when the hydrogel is forced through a 30G needle syringe by moving the plunger of a 1 mL syringe containing the hydrogel at a rate of 100 mm/min for about 11 mm, and measuring the average force from about 4 mm to about 10 mm.

A crosslinked macromolecular matrix may have tunable swelling properties based on reaction conditions and hydrogel dilution. In some embodiments, a crosslinked macromolecular matrix may have a swelling ratio of about 20 to about 200. A swelling ratio is the ratio of the weight of the crosslinked macromolecular matrix after synthesis to the weight of the crosslinked macromolecular matrix without any water. The crosslinked macromolecular matrix may have a swelling power of about 1 to about 7. The swelling power is the ratio of the weight of the crosslinked macromolecular matrix when it is saturated with water to the weight of the crosslinked macromolecular matrix after synthesis.

In a crosslinking reaction, the molecular weight of a hyaluronic acid may vary. In some embodiments, a hyaluronic acid may have a molecular weight of about 200,000 Daltons to about 10,000,000 Daltons, about 500,000 Daltons to about 10,000,000 Daltons, about 1,000,000 Daltons to about 5,000,000 Daltons, or about 1,000,000 Daltons to about 3,000,000 Daltons. When the crosslinking reaction occurs, the resulting crosslinked macromolecular product may have a hyaluronic acid component derived from the hyaluronic acid in the crosslinking reaction. Thus, the ranges recited above may also apply to the molecular weight of a hyaluronic acid component, e.g. about 200,000 Daltons to about 10,000,000 Daltons, about 500,000 Daltons to about 10,000,000 Daltons, about 1,000,000 Daltons to about 5,000,000 Daltons, or about 1,000,000 Daltons to about 3,000,000 Daltons. The term "molecular weight" is applied in this situation to a portion of the matrix even though the hyaluronic acid component may not actually be a separate molecule due to the crosslinking. In some embodiments, a higher molecular weight hyaluronic acid may result in a crosslinked molecular matrix that may have a higher bulk modulus and/or less swelling.

The concentration of hyaluronic acid in an aqueous pre-reaction solution or a crosslinking reaction mixture may vary. In some embodiments, hyaluronic acid is present at about 3 mg/mL to about 100 mg/mL, about 6 mg/mL to about 24 mg/mL, about 1 mg/mL to about 30 mg/mL, about 6 mg/mL, about 9 mg/L, about 12 mg/mL, about 15 mg/L, about 16 mg/mL, about 18 mg/L, about 21 mg/L, or about 24 mg/mL. In some embodiments, higher hyaluronic acid concentration may lead to higher stiffness and/or more swelling in the crosslinked macromolecular matrix.

Any type of collagen may be used in the methods and compositions described herein. In some embodiments, collagen type I, collagen type III, collagen type IV, collagen type VI, or a combination thereof, may be used. In some embodiments, a collagen or a collagen component comprises collagen type I or collagen type III.

A collagen may be derived from cell culture, animal tissue, plant derived or recombinant means or recombinant means thereof, and may be derived from human, porcine, or bovine sources. Some embodiments comprise collagen derived from human fibroblast culture. Some embodiments comprise collagen that has been denatured to gelatin.

Collagen concentration in an aqueous pre-reaction solution or a crosslinking reaction mixture may vary. In some embodiments, collagen may be present at a concentration of about 1 mg/mL to about 40 mg/mL, about 1 mg/mL to about 15 mg/mL, about 3 mg/mL to about 12 mg/mL, about 1.7 mg/mL, about 3 mg/mL, about 6 mg/mL, about 8 mg/mL, or about 12 mg/mL.

In some embodiments, the weight ratio of hyaluronic acid to collagen in an aqueous pre-reaction solution or a aqueous pre-reaction solution or a crosslinking reaction mixture (e.g. [wt hyaluronic acid]/[wt collagen]) may be about 0.5 to about 10, about 1 to about 7, about 0.5 to about 3, about 1 to about 3, about 1 to about 2, about 1, about 2, about 3, about 3.5, about 4, about 5, 5.33, about 6, about 7, or any weight ratio in a range bounded by, and/or between, any of these values. When the crosslinking reaction occurs, the resulting crosslinked macromolecular product may have a collagen component derived from the collagen in the crosslinking reaction. Thus, the resulting crosslinked macromolecular matrix may have a weight ratio of hyaluronic acid component to collagen component that corresponds to the weight ratio in the crosslinking reaction, e.g. about 0.5 to about 10, about 1 to about 7, about 0.5 to about 3, about 1 to about 3, about 1 to about 2, about 1, about 2, about 3, about 3.5, about 4, about 5, about 5.33, about 6, about 7, or any weight ratio in a range bounded by, and/or between, any of these values. A higher weight ratio of hyaluronic acid to collagen may result in a crosslinked macromolecular matrix with increased swelling, decreased stiffness, and/or decreased cell adhesion.

Certain advantageous compositions of the invention include compositions having a hyaluronic acid to collagen weight ratio of about 3:3, about 12:6, about 16:8, about 12:12, about 12:24, about 12:3, about 16:3, or about 20:3 (mg/mL).

In some embodiments, the weight ratio of hyaluronic acid to collagen in an aqueous pre-reaction solution or an aqueous pre-reaction solution or a crosslinking reaction mixture may be about 12 mg/mL of hyaluronic acid to about 6 mg/mL collagen, about 12 mg/mL of hyaluronic acid to about 12 mg/mL collagen, or about 16 mg/mL of hyaluronic acid to about 8 mg/mL collagen. In some embodiments, the collagen may be collagen type 1.

An increase in the amount of both hyaluronic acid and collagen may result in a crosslinked macromolecular matrix with increased stiffness.

A salt may help to screen the negative charges of hyaluronic acid from the positive charges of collagen, and may thus prevent precipitation of a polyionic ion complex from solution. However, high concentrations of salt may reduce the solubility of some components in solution. Thus, in some embodiments, the salt concentration of an aqueous pre-reaction solution or a crosslinking reaction mixture may be high enough to screen the charges so that the polyionic ion complex is not formed, but also low enough so that the components of the mixture remain in solution. For example, the total salt concentration of some aqueous pre-reaction solutions or crosslinking reaction mixtures may be about 10 mM to about 1 M, about 100 mM to about 300 mM, or about 150 mM. In some embodiments, a higher salt concentration may increase the efficiency of a crosslinking reaction, which may result in lower swelling and/or higher stiffness.

Some salts in an aqueous pre-reaction solution or a crosslinking reaction mixture may be non-coordinating buffers. Any non-coordinating buffer may be used that is capable of buffering the mixture and does not form coordinating complexes with coupling agents or metal atoms. Examples of suitable non-coordinating buffers may include, but are not limited to, 2-(N-morpholino)ethanesulfonic acid (MES), 3-(N-morpholino)propanesulfonic acid (MOPS), 4-(2-hydroxyethyl)-1-piperazinyl)ethanesulfonic acid (HEPES), 3-[4-(2-hydroxyethyl)-1-piperazinyl]propanesulfonic acid (HEPPS), N-cyclohexyl-2-aminoethanesulfonic acid (CHES), N-cyclohexyl-3-aminopropanesulfonic acid (CAPS), etc.

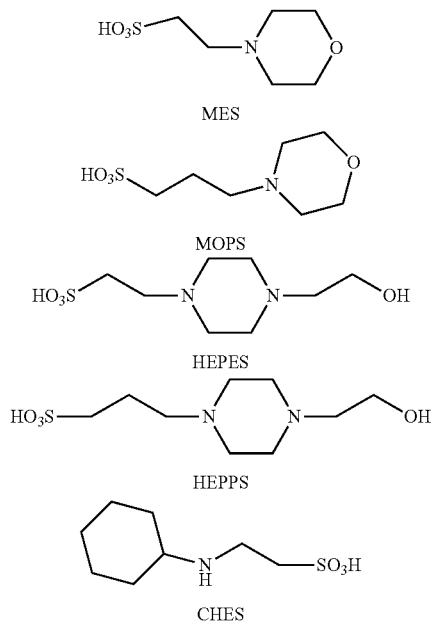

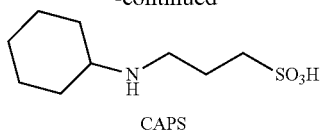

CAPS

The concentration of a non-coordinating buffer may vary. For example, some aqueous pre-reaction solutions or crosslinking reaction mixtures may have a buffer concentration in a range of about 10 mM to about 1 M, about 10 mM to about 500 mM, about 20 mM to about 100 mM, or about 25 mM to about 250 mM. Some aqueous pre-reaction solutions or crosslinking reaction mixtures comprise MES at a concentration of about 20 mM to about 200 mM, about 20 mM to about 100 mM, about 100 mM, or about 180 mM.

Non-buffering salts may also be included in an aqueous pre-reaction solution or a crosslinking reaction mixture as an alternative to, or in addition, to buffering salts. Some examples may include sodium chloride, potassium chloride, lithium chloride, potassium bromide, sodium bromide, lithium bromide, and the like. The concentration of a non-buffering salt may vary. For example, some mixtures may have a non-buffering salt concentration in a range of about 10 mM to about 1 mM, about 30 mM to about 500 mM, or about 50 mM to about 300 mM. In some embodiments, sodium chloride may be present at a concentration in a range of about 0.5% w/v to about 2%, about 0.9% w/v, about 1.6% w/v, about 20 mM to about 1 mM, about 40 mM to about 500 mM, about 50 to 300 mM, about 80 mM to about 330 mM, about 150 mM, or about 270 mM.

The pH of an aqueous pre-reaction solution may be lower than the pH of a crosslinking reaction mixture. If the salt content of the aqueous pre-reaction solution is low, the pH may be lower to enhance solubility of the hyaluronic acid and the collagen. If the salt content is higher, the pH may be higher in the aqueous pre-reaction solution. In some embodiments, the pH of the aqueous pre-reaction mixture is about 1 to about 8, about 3 to about 8, about 4 to about 6, about 4.7 to about 7.4, or about 5.4. For low salt concentrations, the pH may be about 1 to about 4 or about 1 to about 3. In some embodiments, a pH of around 5.4 may result in a crosslinked macromolecular matrix having higher stiffness and/or lower swelling.

In some embodiments, pH may be adjusted to neutral to allow collagen gelation or fiber formation before adding a coupling agent.

In some embodiments, the pH may be adjusted to neutral immediately prior to, around the time of, or after adding a coupling agent, such that collagen gelation is reduced or does not substantially occur.

Any water-soluble coupling agent may be used that can crosslink hyaluronic acid to collagen. Some non-limiting examples of a coupling agent include carbodiimides such as N,N'-dicyclohexylcarbodiimide (DCC), N,N'-diisopropylcarbodiimide (DIC), or 1-ethyl-3-(3-dimethylaminopropyl)carbodiimide (EDC), etc. Carbodiimide coupling agents may facilitate ester or amide bond formation without becoming part of the linkage. In other words, an ester bond or an amide bond may comprise atoms from a carboxylate group from one of hyaluronic acid or collagen, and a hydroxyl group or an amine group from the other. However, other coupling agents that become part of the crosslinking group may be used. The concentration of a coupling agent may vary. In some embodiments, a coupling agent may be present at about 2 mM to about 150 mM, about 2 mM to about 50 mM, about 20 mM to about 100 mM, or about 50 mM. In some embodiments, the coupling agent is EDC that is present at a concentration of about 20 mM to about 100 mM, about 2 mM to about 50 mM, or about 50 mM.

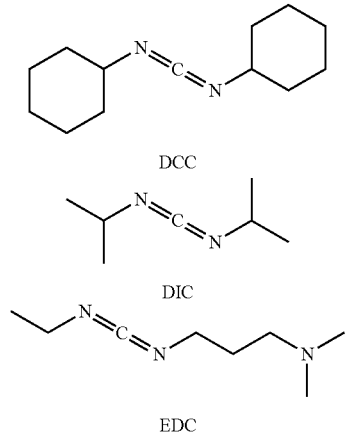

DCC

DIC

EDC

A crosslinking reaction can include any reaction wherein hyaluronic acid is covalently linked to collagen in a plurality of (e.g. more than 1) positions. In some embodiments, a crosslinking reaction may be represented by Scheme 1 below. In Scheme 1, only some of the reacting functional groups are depicted. Additionally, some functional groups may potentially react in a crosslinking reaction, but may remain unreacted. Unreacted functional groups such as these are not shown. For example, OH, CO$_2$H, —NHCOCH$_3$, and other groups on hyaluronic acid that are not shown may react, but may also remain unreacted. Similarly, collagen may have additional groups that may react, but may also remain unreacted, such as OH, SH, CO$_2$H, NH$_2$, etc. Additionally, fewer groups may react than those depicted.

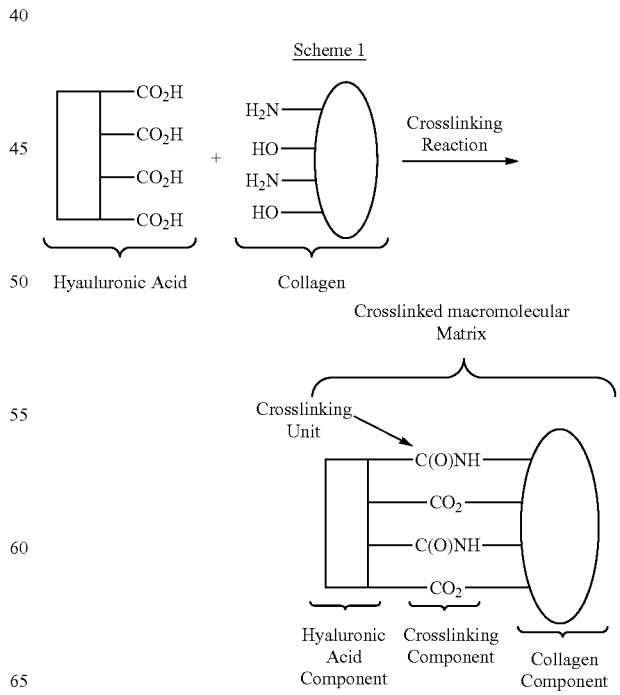

In Scheme 1, functional groups such as $CO_2H$ on hyaluronic acid may react with functional groups on collagen such as $NH_2$ and OH to form several crosslink units. The crosslink units together make up the crosslinking component. In Scheme 1, a coupling component does not become part of a crosslink unit. However, for some coupling agents, at least part of a coupling agent may be incorporated into a crosslink unit. The hyaluronic acid component includes hyaluronic acid that has reacted to become part of a crosslinked macromolecular matrix. The collagen component includes collagen that has reacted to become part of a crosslinked macromolecular matrix. In addition to the crosslinking between hyaluronic acid and collagen, hyaluronic acid or collagen may be partially self-crosslinked. Thus, Scheme 1 is presented for convenience in understanding the crosslinking reaction, but does not necessarily reflect an actual chemical structure. For example, a crosslinked molecular matrix may be a network of hyaluronic acid macromolecules and collagen macromolecules, with many macromolecules crosslinked to more than one macromolecule.

As a result of a crosslinking reaction, a crosslinked macromolecular matrix may comprise a crosslinking component that crosslinks or covalently connects the hyaluronic acid component to the collagen component. As explained above, a crosslink component comprises a plurality of crosslink units, or individual covalent bonding links, between the hyaluronic acid component and the collagen component. A crosslink unit may simply be a direct bond between a hyaluronic acid component and a collagen component, so that the coupling agent may not be incorporated into the crosslinked macromolecular matrix. Alternatively, a crosslink unit may contain additional atoms or groups from the coupling agent such that at least a portion of the coupling agent may become part of the crosslinked macromolecular matrix. At least a portion of the crosslink units comprise an ester bond or an amide bond. In some embodiments, at least a portion of the crosslink units may be —CON— or —$CO_2$—, where the N is a nitrogen from an amino acid residue.

An activating agent may be used to increase the rate of the crosslinking reaction and the number of crosslink units in the final product. In some embodiments, an activating agent may be a triazole such as hydroxybenzotriazole (HOBT) or 1-hydroxy-7-azabenzotriazole (HOAT); a fluorinated phenol such as pentafluorophenol; a succinimide such as N-hydroxysuccinimide (NHS) or N-hydroxysulfosuccinimide (sulfoNHS), and the like.

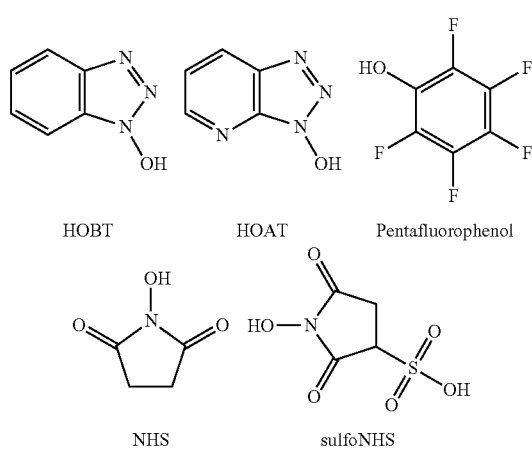

HOBT  HOAT  Pentafluorophenol
NHS  sulfoNHS

The concentration of an activating agent may vary. In some embodiments, the activating agent may have a concentration of about 2 mM to about 200 mM, about 2 mM to about 50 mM, about 20 mM to about 100 mM, or about 50 mM. In some embodiments, the activating agent may be NHS or sulfoNHS at a concentration of about 2 mM to about 50 mM. In some embodiments, the activating agent may be N-hydroxysulfosuccinimide sodium salt at a concentration of about 20 mM to about 100 mM, or about 50 Mm.

In some embodiments, a crosslinking reaction mixture may comprise a carbodiimide coupling agent and an activating agent. In some embodiments, the coupling agent is EDC and the activating agent is NHS or sulfoNHS. In some embodiments EDC is present at a concentration of about 2 mM to about 50 mM and NHS or sulfoNHS is present at about 2 mM to about 50 mM.

In some embodiments, a crosslinking reaction mixture may comprise hyaluronic acid at a concentration of about 3 mg/mL, human collagen type III at a concentration of about 3 mg/mL, 2-(N-morpholino)ethanesulfonic acid at a concentration of about 100 mM, sodium chloride at a concentration of about 0.9 wt % or about 150 mM, 1-ethyl-3-(3-dimethylaminopropyl)carbodiimide at a concentration of about 50 mM, and N-hydroxysulfosuccinimide sodium salt at a concentration of about 50 mM, wherein the solution has a pH of about 5.4.

In some embodiments, a crosslinking reaction mixture may comprise hyaluronic acid at a concentration of about 6 mg/mL, human collagen type III at a concentration of about 6 mg/mL, 2-(N-morpholino)ethanesulfonic acid at a concentration of about 180 mM, sodium chloride at a concentration of about 0.9 wt % or about 150 mM, 1-ethyl-3-(3-dimethylaminopropyl)carbodiimide at a concentration of about 50 mM, and N-hydroxysulfosuccinimide sodium salt at a concentration of about 50 mM, wherein the solution has a pH of about 5.4.

In some embodiments, a crosslinking reaction mixture may comprise hyaluronic acid at a concentration of about 16 mg/mL of, rat collagen type I at a concentration of about 8 mg/mL, 2-(N-morpholino)ethanesulfonic acid at a concentration of about 100 mM, sodium chloride at a concentration of about 0.9 wt % or about 150 mM, 1-ethyl-3-(3-dimethylaminopropyl)carbodiimide at a concentration of about 50 mM, and N-hydroxysulfosuccinimide sodium salt at a concentration of about 50 mM, wherein the solution has a pH of about 5.4.

In some embodiments, a crosslinking reaction mixture may comprise hyaluronic acid at a concentration of about 12 mg/mL, rat collagen type I at a concentration of about 12 mg/mL, 2-(N-morpholino)ethanesulfonic acid at a concentration of about 100 mM, sodium chloride at a concentration of about 0.9 wt % or about 150 mM, 1-ethyl-3-(3-dimethylaminopropyl)carbodiimide at a concentration of about 50 mM, and N-hydroxysulfosuccinimide sodium salt at a concentration of about 50 mM, wherein the solution has a pH of about 5.4.

In some embodiments, a crosslinking reaction mixture may comprise hyaluronic acid at a concentration of about 12 mg/mL, rat tail collagen type I at a concentration of about 12 mg/mL, 2-(N-morpholino)ethanesulfonic acid at a concentration of about 100 mM, sodium chloride at a concentration of about 0.9 wt % or about 150 mM, 1-ethyl-3-(3-dimethylaminopropyl)carbodiimide at a concentration of about 50 mM, and N-hydroxysulfosuccinimide sodium salt at a concentration of about 50 mM, wherein the solution has a pH of about 5.3.

In some embodiments, a crosslinking reaction mixture may comprise hyaluronic acid at a concentration of about 3 mg/mL, human collagen type I at a concentration of about 3 mg/mL, 2-(N-morpholino)ethanesulfonic acid at a concentration of about 100 mM, sodium chloride at a concentration of about 0.9 wt % or about 150 mM, 1-ethyl-3-(3-dimethylaminopropyl)carbodiimide at a concentration of about 50 mM, and N-hydroxysulfosuccinimide sodium salt at a concentration of about 50 mM, wherein the solution has a pH of about 5.4.

In some embodiments, a crosslinking reaction mixture may comprise hyaluronic acid at a concentration of about 12 mg/mL, human collagen type I at a concentration of about 6 mg/mL, 2-(N-morpholino)ethanesulfonic acid at a concentration of about 100 mM, sodium chloride at a concentration of about 0.9 wt % or about 150 mM, 1-ethyl-3-(3-dimethylaminopropyl)carbodiimide at a concentration of about 50 mM, and N-hydroxysulfosuccinimide sodium salt at a concentration of about 50 mM, wherein the solution has a pH of about 5.4.

In some embodiments, a crosslinking reaction mixture may comprise hyaluronic acid at a concentration of about 16 mg/mL, human collagen type I at a concentration of about 8 mg/mL, 2-(N-morpholino)ethanesulfonic acid at a concentration of about 100 mM, sodium chloride at a concentration of about 0.9 wt % or about 150 mM, 1-ethyl-3-(3-dimethylaminopropyl)carbodiimide at a concentration of about 50 mM, and N-hydroxysulfosuccinimide sodium salt at a concentration of about 50 mM, wherein the solution has a pH of about 5.4.

In some embodiments, a crosslinking reaction mixture may comprise hyaluronic acid at a concentration of about 12 mg/mL, human collagen type I at a concentration of about 12 mg/mL, 2-(N-morpholino)ethanesulfonic acid at a concentration of about 100 mM, sodium chloride at a concentration of about 0.9 wt % or about 150 mM, 1-ethyl-3-(3-dimethylaminopropyl)carbodiimide at a concentration of about 50 mM, and N-hydroxysulfosuccinimide sodium salt at a concentration of about 50 mM, wherein the solution has a pH of about 5.4.

In some embodiments, a crosslinking reaction mixture may comprise hyaluronic acid at a concentration of about 24 mg/mL, human collagen type I at a concentration of about 12 mg/mL, 2-(N-morpholino)ethanesulfonic acid at a concentration of about 100 mM, sodium chloride at a concentration of about 0.9 wt % or about 150 mM, 1-ethyl-3-(3-dimethylaminopropyl)carbodiimide at a concentration of about 50 mM, and N-hydroxysulfosuccinimide sodium salt at a concentration of about 50 mM, wherein the solution has a pH of about 5.4.

In some embodiments, a crosslinking reaction mixture may comprise hyaluronic acid at a concentration of about 16 mg/mL, human collagen type I at a concentration of about 3 mg/mL, 2-(N-morpholino)ethanesulfonic acid at a concentration of about 100 mM, sodium chloride at a concentration of about 0.9 wt % or about 150 mM, 1-ethyl-3-(3-dimethylaminopropyl)carbodiimide at a concentration of about 50 mM, and N-hydroxysulfosuccinimide sodium salt at a concentration of about 50 mM, wherein the solution has a pH of about 5.4.

In some embodiments, a crosslinking reaction mixture may comprise hyaluronic acid at a concentration of about 9 mg/mL, human collagen type I at a concentration of about 3 mg/mL, 2-(N-morpholino)ethanesulfonic acid at a concentration of about 100 mM, sodium chloride at a concentration of about 0.9 wt % or about 150 mM, 1-ethyl-3-(3-dimethylaminopropyl)carbodiimide at a concentration of about 50 mM, and N-hydroxysulfosuccinimide sodium salt at a concentration of about 50 mM, wherein the solution has a pH of about 5.4.

In some embodiments, a crosslinking reaction mixture may comprise hyaluronic acid at a concentration of about 12 mg/mL, human collagen type I at a concentration of about 3 mg/mL, 2-(N-morpholino)ethanesulfonic acid at a concentration of about 100 mM, sodium chloride at a concentration of about 0.9 wt % or about 150 mM, 1-ethyl-3-(3-dimethylaminopropyl)carbodiimide at a concentration of about 50 mM, and N-hydroxysulfosuccinimide sodium salt at a concentration of about 50 mM, wherein the solution has a pH of about 5.4.

In some embodiments, a crosslinking reaction mixture may comprise hyaluronic acid at a concentration of about 15 mg/mL, human collagen type I at a concentration of about 3 mg/mL, 2-(N-morpholino)ethanesulfonic acid at a concentration of about 100 mM, sodium chloride at a concentration of about 0.9 wt % or about 150 mM, 1-ethyl-3-(3-dimethylaminopropyl)carbodiimide at a concentration of about 50 mM, and N-hydroxysulfosuccinimide sodium salt at a concentration of about 50 mM, wherein the solution has a pH of about 5.4.

In some embodiments, a crosslinking reaction mixture may comprise hyaluronic acid at a concentration of about 18 mg/mL, human collagen type I at a concentration of about 3 mg/mL, 2-(N-morpholino)ethanesulfonic acid at a concentration of about 100 mM, sodium chloride at a concentration of about 0.9 wt % or about 150 mM, 1-ethyl-3-(3-dimethylaminopropyl)carbodiimide at a concentration of about 50 mM, and N-hydroxysulfosuccinimide sodium salt at a concentration of about 50 mM, wherein the solution has a pH of about 5.4.

In some embodiments, a crosslinking reaction mixture may comprise hyaluronic acid at a concentration of about 21 mg/mL, human collagen type I at a concentration of about 3 mg/mL, 2-(N-morpholino)ethanesulfonic acid at a concentration of about 100 mM, sodium chloride at a concentration of about 0.9 wt % or about 150 mM, 1-ethyl-3-(3-dimethylaminopropyl)carbodiimide at a concentration of about 50 mM, and N-hydroxysulfosuccinimide sodium salt at a concentration of about 50 mM, wherein the solution has a pH of about 5.4.

In some embodiments, a crosslinking reaction mixture may comprise hyaluronic acid at a concentration of about 9 mg/mL, human collagen type I at a concentration of about 6 mg/mL, 2-(N-morpholino)ethanesulfonic acid at a concentration of about 100 mM, sodium chloride at a concentration of about 0.9 wt % or about 150 mM, 1-ethyl-3-(3-dimethylaminopropyl)carbodiimide at a concentration of about 50 mM, and N-hydroxysulfosuccinimide sodium salt at a concentration of about 50 mM, wherein the solution has a pH of about 5.4.

In some embodiments, a crosslinking reaction mixture may comprise hyaluronic acid at a concentration of about 15 mg/mL, human collagen type I at a concentration of about 6 mg/mL, 2-(N-morpholino)ethanesulfonic acid at a concentration of about 100 mM, sodium chloride at a concentration of about 0.9 wt % or about 150 mM, 1-ethyl-3-(3-dimethylaminopropyl)carbodiimide at a concentration of about 50 mM, and N-hydroxysulfosuccinimide sodium salt at a concentration of about 50 mM, wherein the solution has a pH of about 5.4.

In some embodiments, a crosslinking reaction mixture may comprise hyaluronic acid at a concentration of about 18 mg/mL, human collagen type I at a concentration of about 6 mg/mL, 2-(N-morpholino)ethanesulfonic acid at a concentration of about 100 mM, sodium chloride at a concentration of about 0.9 wt % or about 150 mM, 1-ethyl-3-(3-dimethylaminopropyl)carbodiimide at a concentration of about 50 mM, and N-hydroxysulfosuccinimide sodium salt at a concentration of about 50 mM, wherein the solution has a pH of about 5.4.

In some embodiments, a crosslinking reaction mixture may comprise hyaluronic acid at a concentration of about 21 mg/mL, human collagen type I at a concentration of about 6 mg/mL, 2-(N-morpholino)ethanesulfonic acid at a concentration of about 100 mM, sodium chloride at a concentration of about 0.9 wt % or about 150 mM, 1-ethyl-3-(3-dimethylaminopropyl)carbodiimide at a concentration of about 50 mM, and N-hydroxysulfosuccinimide sodium salt at a concentration of about 50 mM, wherein the solution has a pH of about 5.4.

In some embodiments, a crosslinking reaction mixture may comprise hyaluronic acid at a concentration of about 1 mg/mL to about 20 mg/mL, porcine collagen type I at a concentration of about 1 mg/mL to about 15 mg/mL, 2-(N-morpholino)ethanesulfonic acid at a concentration of about 20 mM to about 200 mM, sodium chloride at a concentration of about 0.5 wt % to about 2 wt % or about 80 mM to about 330 mM, 1-ethyl-3-(3-dimethylaminopropyl)carbodiimide at a concentration of about 20 mM to about 100 mM, and N-hydroxysulfosuccinimide sodium salt at a concentration of about 20 mM to about 100 mM, wherein the solution has a pH of about 4 to about 6.

In some embodiments, a hydrogel composition as described herein may include a hyaluronic acid:collagen weight ratio of 3 to 1. The concentrations of hyaluronic acid can be from about 12 mg/mL to about 24 mg/mL and the collagen can be from about 3 mg/mL to about 12 mg/mL. The collagen may be collagen type 1. Further, the hydrogel composition may be used for fat grafting applications as an additive. The source of the collagen can vary, but can be human recombinant (cell derived or plant derived), porcine, bovine or ovine. The hydrogels can be formed with an EDC crosslinker and NHS as an activating agent.

Hydrogel compositions described herein can further have a storage modulus (G') and a loss modulus (G") each independently between about 500 Pa and about 4,000 Pa.

A general method of making hydrogel compositions as described herein can be achieved as follows. First, lyophilized hyaluronic acid fibers can be added to a concentrated (e.g. hydrated) collagen solution. The pH can then be managed by the addition of one or more buffer salt and/or the addition of a base (e.g. NaOH). After the pH has been managed, the mixture can be hydrated and thoroughly mixed followed by addition of crosslinking agents. The crosslinking agents can be solids (e.g. powder). The hyaluronic acid and collagen can be left to react. Once reacted, the resultant gel can be particle sized through a filter mesh (e.g. 100 μm) and can be dialyzed with buffer to purify (e.g. against any unused or unreacted crosslinker). The gel can then be sterilized (e.g. using isopropanol). This sterilization can also occur prior to purification. Once sterilized the gel may be ready for administration. The sterilized gel can also be further mixed within adipose tissue or fat cells (e.g. human).

The sterilized gel, either mixed with adipose tissue or not mixed with adipose tissue, can be administered as described herein to treat a condition of, for example, the face, breast, hands, etc.

Additives can also include one or more biocompatible materials suitable to be delivered by the devices described herein. Biocompatible materials include, but are not limited to, dermal fillers, hyaluronic acid-based dermal fillers (e.g. Juvèderm™ Ultra and Juvèderm™ Ultra Plus (Allergan, Irvine, Calif.)), hydrogels (i.e. superabsorbent natural or synthetic polymers), organogels, xerogels, encapsulated and/or cross-linked biomaterials, silicones, glycosaminoglycans (e.g. chondroitin sulfate, dermatin sulfate, dermatin, dermatin sulfate, heparin sulfate, hyaluronic acid, o-sulfated hyaluronic acid), polysaccharides (e.g. chitosan, starch, glycogen, cellulose), collagen, elastin, local anesthetics (e.g. Benzocaine, Chloroprocaine, Cyclomethycaine, Dimethocaine/Larocaine, Propoxycaine, Procaine/Novocaine, Proparacaine, Tetracaine/Amethocaine, Amino amides, Articaine, Bupivacaine, Carticaine, Cinchocaine/Dibucaine, Etidocaine, Levobupivacaine, Lidocaine/Lignocaine, Mepivacaine, Piperocaine, Prilocalne, Ropivacaine, Trimecaine), drugs, bioactive agents, antioxidants, enzyme inhibitors (e.g. anti-hyaluronidase), vitamins, minerals, water, saline, light curable or light activated materials, vaccines, and pH curable or pH activated materials.

Additives can also include bioactive agents. Bioactive agents can augment the mixture either during delivery (e.g. to reduce extrusion force) or after delivery (e.g. to aid in foreign body acceptance). Bioactive agents may include anti-proliferatives including, but not limited to, macrolide antibiotics including FKBP-12 binding compounds, estrogens, chaperone inhibitors, protease inhibitors, protein-tyrosine kinase inhibitors, leptomycin B, peroxisome proliferator-activated receptor gamma ligands (PPARγ), hypothemycin, nitric oxide, bisphosphonates, epidermal growth factor inhibitors, antibodies, proteasome inhibitors, antibiotics, anti-inflammatories, anti-sense nucleotides and transforming nucleic acids. Drugs can also refer to bioactive agents including anti-proliferative compounds, cytostatic compounds, toxic compounds, anti-inflammatory compounds, anti-fungal agents, steroids, chemotherapeutic agents, analgesics, antibiotics, protease inhibitors, statins, nucleic acids, polypeptides, growth factors and delivery vectors including recombinant micro-organisms, liposomes, and the like. Combinations of additional bioactive agents are also within the scope of the present description.

In one embodiment, the volume ratio of fat to additive can vary depending on the intended site of delivery of the composition. For example, the ratio of fat to additive can be about 50:1, about 20:1, about 10:1, about 9:1, about 8:1, about 7:1, about 6:1, about 5:1, about 4:1, about 3:1, about 2:1, about 1:1, about 1:2, about 1:3, about 1:4, about 1:5, about 1:6, about 1:7, about 1:8, about 1:9, about 1:10, about 1:20, about 1:50, at least about 2:1, at least about 5:1, at most about 20:1, between about 2:1 and about 5:1, between about 1:5 and about 1:1, between about 1:1 and about 5:1, between about 1:1 and about 10:1, between about 2:1 and about 10:1, between about 3:1 and about 5:1, or between about 4:1 and about 5:1. In one embodiment, the ratio of fat to additive can be between about 2:1 and about 5:1.

When injected or implanted in vivo, the fat/additive hydrogel composition may promote cell and/or tissue growth, including growth into the implant material. For example, a fat/additive composition may stimulate angiogenesis, neovascularization, adipogenesis, collagenesis, cell infiltration, tissue integration, and the like in vivo. Once injected or implanted into a soft tissue using the devices described herein, a fat/additive may stimulate angiogenesis, neovascularization, adipogenesis, and/or collagenesis.

Depending on the particular application of a given device, it may be important for the devices described herein to be sterilized routinely by means commonly known in the art. Therefore, the components of the devices may be made of materials that are known to withstand sterilization techniques such as, but not limited to, dry heat, steam (autoclave), ethylene oxide treatment, gamma radiation, ultra violet (UV) light or combinations thereof including other methods known in the art. The devices can also be constructed of materials that can be cleaned with soap and water or antiseptic materials.

Mixing Devices

In one embodiment, systems are described that can include containers for the collection, processing, and re-injection of fat. In some embodiments, these containers can be flexible, such as flexible bags. The flexible bags can be made of any compliant biocompatible material.

In one embodiment, this material is plastic. However, other materials such as metals or textiles can be used. When used, plastics can include, but are not limited to, polyvinyl chloride (PVC), ethylene vinyl acetate (EVA), polypropylene (PP), combinations thereof, or any other suitable material.

The containers can include two or more distinct compartments. For example, the containers can be compartmentalized containers including at least a first, a second and a third compartment and each compartment can be configured to perform or aid in a function of the systems described.

As illustrated in FIG. 1, system 100 comprises bag 102 made up of first compartment 104, second compartment 106, third compartment 108, and fourth compartment 110. These compartments can be connected in-line.

In use, bag 102 may be suspended by suitable attachment mechanism such as appendage 112. Bag 102 may be suspended such that first compartment 104, second compartment 106, third compartment 108, and fourth compartment 110 are gravity fed.

Harvested, for example freshly harvested, and unprocessed fat enters first compartment 104 either by an in-line flow 114 or manual syringe injection through port 116. The function of first compartment 104 can be to receive and optionally process the fat.

In some embodiments, the bag can be connected in-line, or directly to, a harvesting device such as a liposuction tool, for expedient processing.

Processing of the fat can include removing unnecessary fluids and oils. Processing can be accomplished through the use of a filter. For example, filter 118 may be included at the downstream end or port 120 of first compartment 104. Filter 118 or another mechanism can be configured to separate adipose tissue from unwanted fluids and materials.

After processing in first compartment 104, the processed fat is moved to the second compartment 106 through optional filter 118.

In one embodiment, a user of system 100 breaks frangible seal 122 separating first compartment 104 and second compartment 106 to enable flow 124 of processed fat from first compartment 104 to second compartment 106. In the illustrated example embodiment, only clean, processed adipose tissue is able to enter second compartment 106 through filter 118.

Second compartment 106 may contain one or more additives. The additive(s) may be contained in pouch 126 within or connected to second compartment 106. In some embodiments, pouch 126 can be "popped" by the user or otherwise broken open. Once opened, pouch 126 can release a fixed amount of additive into second compartment 106. In other embodiments, additive can be injected into second compartment 106 through port 128.

Processed fat can also be removed from second compartment 106 through port 130 either before being subjected to additive or after being subjected to additive. In some embodiments, processed fat without additive may be desired.

In some embodiments, a user can manually mix the processed adipose tissue with the additive(s) by shaking, massaging the container, or the like. In one embodiment, a magnetic stir bar can be included in second compartment 106 and spun using a magnetic stirring plate.

In some embodiments, further mixing may be required. In other embodiments, manual mixing may not be used and therefore other types of mixing may be required. In one embodiment, a user can massage the fat and additive mixture through a torturous path 132 within third compartment 108. In other embodiments, the mixture can proceed through torturous path 132 by gravity. As indicated, third compartment 108 can be optional. When used, torturous path 132 can act as a mixing element to standardize the mixing of processed fat with an additive(s).

Tortuous path 132 can be of any configuration that provides mixing of fat and additive. For example, torturous path 132 can have one, two, three, four, five, six, seven, eight, nine, ten, eleven, twelve, more than two, more than three, more than four, more than five, more than six, more than seven, more than eight, more than nine, more than ten, more than eleven, or more than twelve sharp turns. A sharp turn can be a turn of at least 30 degrees, at least 45 degrees, at least 60 degrees, at least 75 degrees, at least 90 degrees, at least 105 degrees, at least 120 degrees, at least 135 degrees, at least 150 degrees, at least 165 degrees, or at least 180 degrees. In one embodiment, torturous path 132 can have at least six sharp turns of at least 90 degrees.

Once fat product has reached the fourth compartment 110, downstream of the tortuous path 132, the user can be assured the fat and additive mixture has been thoroughly mixed. The fourth compartment 110 can be used to deliver mixed product to a patient. The fat/additive mixture can be dispensed from outlet 134 by means of a constant flow of mixture such as through an IV. In other embodiments, fat/additive mixture can be withdrawn from fourth compartment 110 through one of at least on port 136 into a syringe.

In another embodiment, described is an injection device for fat grafting procedures. The device, in one embodiment, is an electromechanical injector device that can mix adipose tissue with additives and then inject the mixture into a patient for tissue augmentation, breast augmentation or reconstruction, dermal filling or other tissue bulking purposes. In another embodiment, the device is a manual injector device that can mix adipose tissue with additives and then inject the mixture into a patient for tissue augmentation, breast augmentation or reconstruction, dermal filling or other tissue bulking purposes.

The electromechanical injector devices described herein can allow an operator to easily inject the mixture through any size needle known in the art by depressing a button. The electromechanical injector devices are easy to hold, manipulate and operate with one hand, and in some cases adjust easily with the operator's opposing hand. The electromechanical injector devices can allow the operator to precisely control the injection speed (or extrusion rate) of the mixture being injected. The electromechanical injector devices can also indicate the initial volume, volume injected and remaining volume of the mixture being delivered to a patient.

The electromechanical injector devices described herein comprise an outer shell. The outer shell has an ergonomic shape that allows the operator to hold and manipulate the device easily. Unlike traditional syringes which do not conform to any ergonomic aspect of the hand, the present devices can have at least one ergonomic design shaped into the outer shell of the device. Additionally, the present devices can accommodate operator hands of different sizes. Hand size accommodation can be accomplished by different device sizes, position-adjustable device handgrips or interchangeable device handgrips. For example, interchangeable device handgrips can come in various predetermined sizes or can be personalized for a particular user. In one embodiment, the device handgrip can slide along a rail forward or backward relative to the outer shell and be locked into place. In another embodiment, the device handgrip can be unlocked, removed and re-attached in another position on the outer shell. Additionally, the outer shell can be sized for a particular user.

The outer shell of the electromechanical injector devices described herein can be comprised of materials such as, but not limited to, rigid thermoplastics, thermoplastic elastomers, silicones, glass, metals, composite materials, carbons fillers, or any combination thereof.

The electromechanical injector devices may have at least a portion sealed to prevent fluids or debris from entering the inner body of the device. Methods of sealing a medical device of this type are known in the art and can include, but are not limited to, o-rings, gaskets, sealants, silicones, thermoplastic elastomers, polymers, polymer coatings, sheaths, partial sheaths and waxes. The external buttons described infra may be sealed to prevent fluids or debris from entering the inner body of the device through the buttons location.

An injection device, such as electromechanical injection device 200 in FIG. 2, can include first cartridge, chamber or compartment 202 configured to contain adipose tissue and second compartment 204 configured to contain an additive. In some embodiments, the device may not include a motor and may be manually progressed.

Electromechanical injection device 200 may include one or more of the following components used to inject a mixture into a patient: vacuum pump(s), air pump(s), motor(s) (e.g. gear or step motor), gear(s) (e.g. rack and pinion system or worm gear), linear actuator(s), plunger(s), linear spine shaft(s), leadscrew(s), linear guide(s), mixing chamber(s), air piston(s), spring(s) (e.g. compression), magnet(s) and/or replaceable compressed air cartridge(s).

Electromechanical injection device 200 can include one or more motors or actuators to move internal components. The motor(s) and/or actuator(s) can drive one or more leadscrews and can be driven by an appropriate voltage. The motor can have a maximum stall torque of 7,500 g cm, 5,000 g cm, or 4,480 g cm. The stall torque can have a minimum of 100 g/cm, 250 g/cm, or 396 g/cm. The maximum efficiency torque can have a maximum of 1,500 g/cm, 1,000 g/cm, or 900 g/cm. The maximum efficiency torque can have a minimum of 50 g/cm, 75 g/cm, or 88 g/cm. Further, the gear ratio of the motor and/or actuator can have a maximum of about 500:1, 350:1, or 300:1. The gear ratio of the motor and/or actuator can have a minimum of about 10:1, 25:1, 30:1, or 100:1. In one embodiment, the gear ratio can be about 298:1. In one embodiment, the motor is a Firgelli GM12-N20VA-08260-298-R gearmotor (Firgelli Technologies, Inc. Victoria, BC, Canada).

Electromechanical injection device 200 can include drive mechanism including first movable plunger 206 in first compartment 202 and a second movable plunger 208 in second compartment 204. The drive mechanism can include a first motor 210 operatively coupled to first plunger leadscrew 212 and a second motor 214 operatively coupled to second plunger leadscrew 216. In some embodiments, a single motor may be used to drive both first plunger leadscrew 212 and second plunger leadscrew 216. Electromechanical injection device 200 can further include a mixing chamber 218 configured to receive and mix the adipose tissue and the additive upon operation of the drive mechanism.

Mixing chamber 218 can include a tortuous path. Tortuous path can be of any configuration that provides mixing of adipose tissue and additives. For example, torturous path can have one, two, three, four, five, six, seven, eight, nine, ten, eleven, twelve, more than two, more than three, more than four, more than five, more than six, more than seven, more than eight, more than nine, more than ten, more than eleven, or more than twelve sharp turns. A sharp turn can be a turn of at least 30 degrees, at least 45 degrees, at least 60 degrees, at least 75 degrees, at least 90 degrees, at least 105 degrees, at least 120 degrees, at least 135 degrees, at least 150 degrees, at least 165 degrees, or at least 180 degrees.

Electromechanical injection device 200 further comprises a connector 220, for example, a luer connector for coupling the device with a needle 222 or cannula distal to mixing chamber 218.

Electromechanical injection device 200 may also include a printed circuit board (PCB) 224 including a processor and memory with one or more algorithms for receiving user input to activate or stop the drive mechanism, for enabling control of injection rate, mixing ratio between adipose tissue and additive, or any other useful function.

PCB 224 can control the display screen, pump, motor, linear actuator and/or other powered components. The PCB can be used to regulate the current and/or voltage delivered to the various electronic parts of the devices.

Figure 3A:
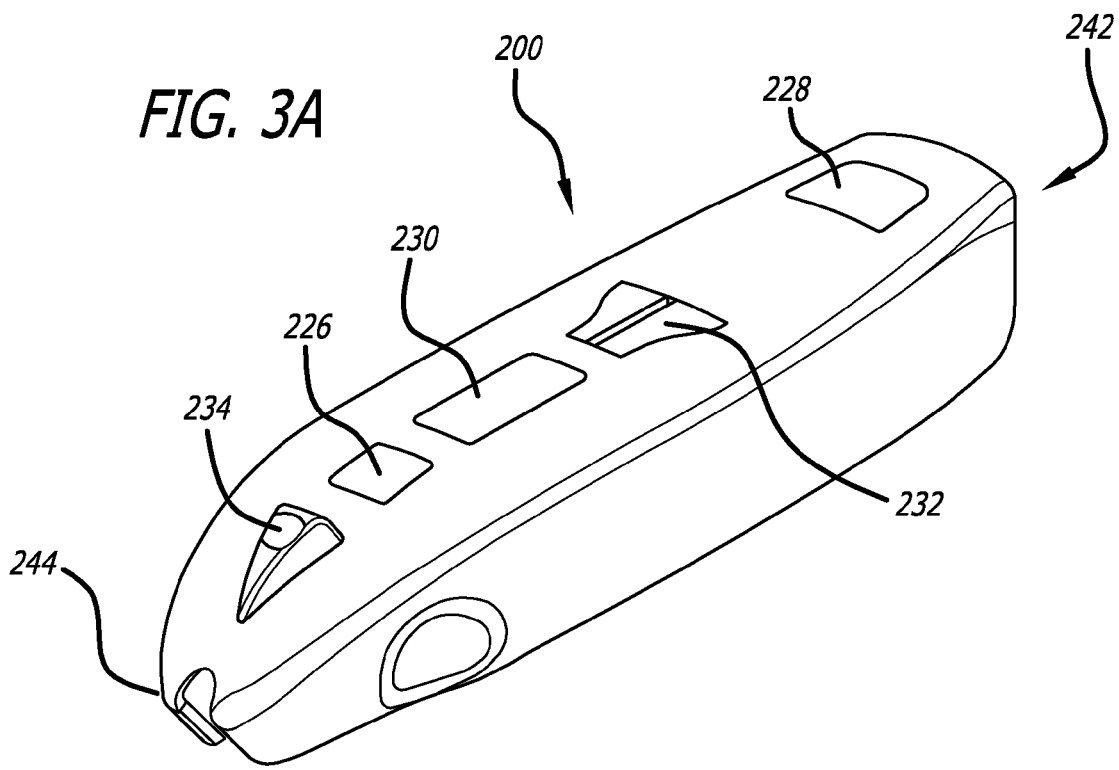
FIGS. 3A and 3B, respectively, illustrate an exemplary electromechanical injection device and accompanying base station.
Figure 3B:
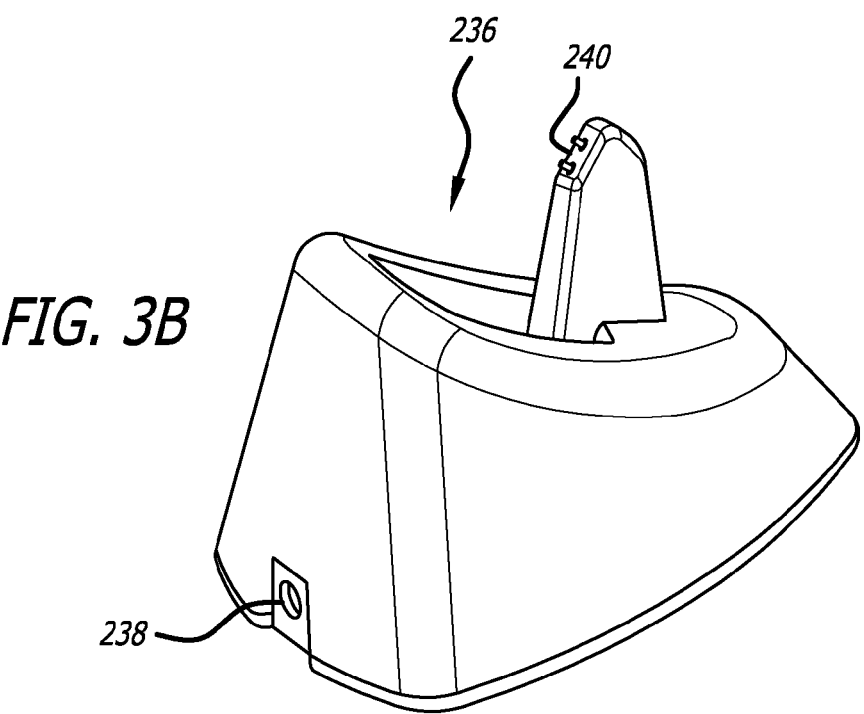

FIG. 3 illustrates an example of an external shape of electromechanical injection device 200 and an optional charging station for the device.

Electromechanical injection device 200 can include an inject button 226, a power button 228 to power on and off the processor(s) and motor(s), a display 230 for menu navigations and status, navigation buttons 232, and a cartridge eject button 234.

Display 230 can include those commonly known in the art that are easily viewable by the operator including, but not limited to, organic light-emitting diode (OLED), light emitting diode (LED) or liquid crystal display (LCD). Display 230 can display information about the device, about the adipose tissue, about the additive, about the mixture and/or about the injection itself. The screen can display some or all of the following, non-limiting, example information: company name and/or logo, device name, fat cell name, additive name, device part number, fat cell lot number, fat cell reference number, additive lot number, fat cell lot number, fat cell reference number, reference number, device lot number, additive and/or fat cell volume, additive and/or fat cell expiration date, mixture volume, mixture volume injected into a specific anatomy of the patient, mixture injection speed, depth of injection, needle force, needle gauge, needle length, patient name, patient identification, location of injection (patient's anatomy), date, time, language, number of uses or injections (until battery needs recharging or replacement), device status (e.g. ready, cartridge not loaded, cartridge empty, error), firmware version, power status (on, off, standby), battery power, battery power remaining, and/or battery charging status.

The information portrayed on display 230 may be displayed on the primary menu screen or on one or more user-selectable or user-configurable menu screens. The operator may easily customize the screen.

Electromechanical injection device 200 can have different dilution and speed settings or can have one pre-set dilution and speed setting, and may be integrated with fat harvesting and processing stages that are executable by the processor. Electromechanical injection device 200 may be battery powered or powered from an external source such as from a conventional power plug. The device may display the total amount of fat and additive injected into an individual and give warnings in the event a malfunction was to occur.

Electromechanical injection device 200 can be fitted with speaker 246 driven by power source 248 and controlled by PCB 224. Speaker 246 can produce audible tones when the device needs attention. Such instances that may require attention include, but are not limited to, low battery power, empty cartridge, confirmation of a setting, power on and power off.

Electromechanical injection device 200 may require power source 248 to operate. Power source 248 can be supplied by such means as a direct connection to an AC/DC power source, this can be accomplished using an electrical plug. Using a direct connection to a power source as described above requires that the devices be restrained by the power cord. In one embodiment, the devices can be powered by one or more batteries. The batteries may be common non-rechargeable types such as, but not limited to, A, AA, AAA, C, D, and 9V. The one or more batteries used may be rechargeable batteries. The rechargeable battery(s) can be charged through induction or through direct-connect interface to an AC/DC power source. In one embodiment, the rechargeable battery(s) may be a permanent battery that charges within the devices and is not removed by the operator. The rechargeable battery(s) may be semi-permanent meaning they are charged inside the devices, but can be replaced if the battery(s) expire or malfunction over time. The rechargeable battery(s) may be operator replaceable of either standard or non-standard type batteries. The operator replaceable rechargeable batteries may be charged within the devices or outside the devices. The operator replaceable rechargeable batteries charged outside the devices can be specific for the devices and comprise a series of standby batteries ready for rapid swapping.

Electromechanical injection device 200 can include a base station 236 for charging. Base station 236 can include a power port 238 configured to accept power from an external source such as from a conventional power plug. Further, base station 236 can include charging contacts 240 that can engage a charging port (not illustrated) on or within the distal end 242 of electromechanical injection device 200 so that proximal end 244 stands straight up in the air when the device is charging.

Base station 236 can function as a convenient place to store electromechanical injection device 200 when it is not in use. A base station may comprise multiple electromechanical injection devices. Base station 236 can further include a port (e.g. USB, firewire) from which data can be transferred to and from a device's internal or external storage or devices housed in the stand. The data can be synchronized with database software stored on a standalone or networked computer. Base station 236 may further comprise the components to wirelessly network electromechanical injection device 200 and its data contents for retrieval wirelessly throughout a network.

Electromechanical injection device 200 can include one or more elements configured for storage. The storage can be built-in internal storage (e.g. random access memory, flash memory, read only memory, microdrive). The internal storage may be built directly into the PCB. The storage can be an external source. The device can comprise a slot to which an external storage device may be connected or inserted. Such external storage devices include, but are not limited to universal serial bus (USB) drives, firewire drives, flash and media cards, and microdrives.

The internal or external storage can contain information about the device and/or adipose tissue, additives, or mixture thereof. The information can include, but is not limited to, operating software, firmware, device usage statistics, patient information, patient name, patient identification, fat cell name, fat cell reference number, additive name, additive reference number, additive Rx number, additive lot number, additive expiration date, fat cell expiration date, date of injection(s), time of injection(s), area(s) of injection(s), injection volume(s), injection volume(s) per area injected, total volume injected, and operator name.

Electromechanical injection device 200 may have the ability to drive a motor at variable speeds to facilitate different rates of delivery of the mixtures. A processor can have the ability to run a motor in both rotational directions. Additionally, electromechanical injection device 200 may have sensors to quantify the velocity of a leadscrew and verify the desired delivery rate. The sensors may provide feedback to the processor allowing it to drive the motor faster or slower if the desired delivery rate is not being met.

In one embodiment, upon actuation of inject button 226, a signal can be sent to the processor and therein the software may drive the motor forward at the proper velocity for the desired injection rate. The software can implement one or more algorithms to maintain the injection rate during variations in resistance from a leadscrew.

In one embodiment, upon release of inject button 226, the software and processor can drive a motor in reverse to full speed for a predetermined distance in order to release pressure on first compartment 202 or second compartment 204. This can allow for more precise delivery of a mixture and can prevent leaking.

In one embodiment, in the event that the processor detects the entire contents of first compartment 202 and/or second compartment 204 have been expelled, the processor can reverse the motor as described above and present an "empty container" warning on the display.

In one embodiment, upon detection by the processor, based on feedback from sensors, that the desired injection rate cannot be attained, the motor may reverse as though inject button 226 was released, and a warning message may be displayed. This situation could result from situations such as, but not limited to, an improperly inserted container, a blockage preventing delivery of the mixture, a mechanical failure or combinations thereof.

In some embodiments, the devices described herein can deliver mixtures or inject into areas of tissue that require high precision. As such, the devices can have one or more, in some cases two or more, sensors which monitor the device's precision. In some embodiments, the sensors or systems can be redundant.

In some embodiments, the mixtures, even more specifically, the additives to be delivered may be non-Newtonian or mixtures of Newtonian and non-Newtonian fluids. An example additive that may have non-Newtonian dynamics can be hyaluronic acid based additives. Such fluids can have inconsistent and/or unpredictable force-to move requirements which may utilize the redundant features described above. Such products can have high yield points requiring high stall torque requirements. Non-Newtonian fluids may have high yield points but have rapid drops in force-to-move requirements after the yield point is overcome. As such, the devices described herein can accommodate for rapid changes in extrusion force requirements.

In one embodiment, the devices can achieve a steady state of mixture delivery despite the changes in fluid consistency and/or viscosity, including differing yield points. As such, the devices can be equipped with PCBs that can constantly monitor the delivery force, speed, and container pressure, etc. In addition, devices may be designed such that the plunger(s) (e.g., 206, 208) may be backed up at the termination of mixture dispensation in order to avoid over-dispensing due to, for example, pressure build up during administration.

In another embodiment, a system for mixing adipose tissue and at least one additive includes a multi-purpose syringe. An exemplary syringe, syringe 400 is illustrated in FIGS. 4A-E. Syringe 400 can include a first section 402 and a second section 404. Second section 404 can be separable and connectable to first section 402. First section 402 and second section 404 may be coupled together by mating threads, clips, or a pressure fit.

First section 402 can include a body portion 406 into which a plunger 408 having a plunger head 410 is inserted. Plunger 408 and plunger head 410 are slidable within body section 406 and can operate as a syringe piston.

Second section 404 can include multiple, replaceable units. Each replaceable unit includes at least one feature that performs a particular function of the fat grafting process.

Figure 4A:
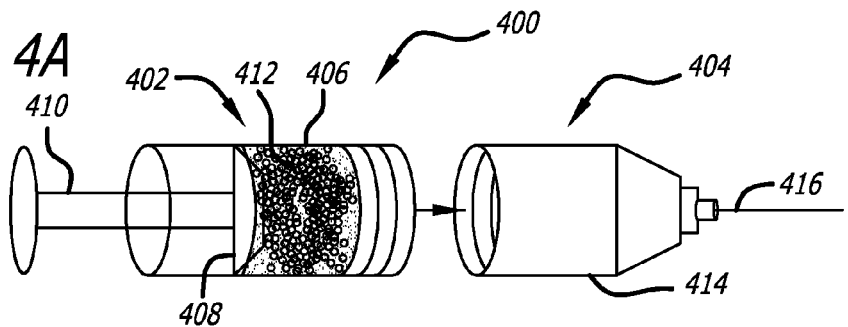
FIGS. 4A-4E illustrate an exemplary multi-purpose syringe system as described.

In FIG. 4A, adipose tissue 412, along with other extracted components are shown in body portion 406. Second section 404 is illustrated with first replaceable unit 414 including a cannula and/or needle 416 that can be used to harvest adipose tissue 412. After harvesting, first replaceable unit 414 is removed.

Figure 4B:
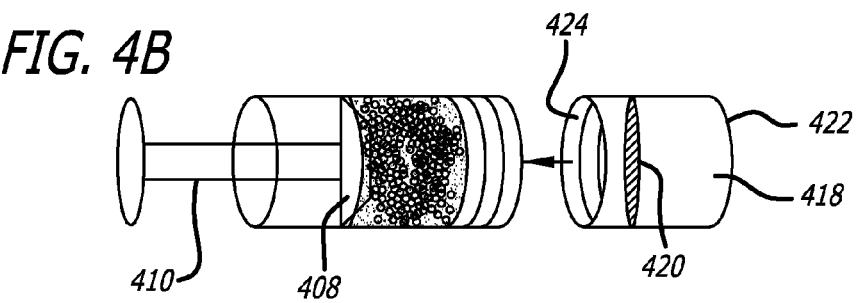

In FIG. 4B, second section 404 is a second replaceable unit 418 containing a filter or filters 420 that can be attached to first section 402. The filter(s) 420 can be optimized so that the majority of harvested adipose tissue will not pass through the filter while other lipoaspirate fluids extracted with the fat will pass through, the majority of harvested tissue can be greater than about 60%, about 70%, about 80%, about 90%, or about 100%. Distal end 422 of second replaceable unit 418 can be open to allow the lipoaspirate to flow and the filters can be nearest proximal end 424 to maximize retention of fat in the top section.

Figure 4C:
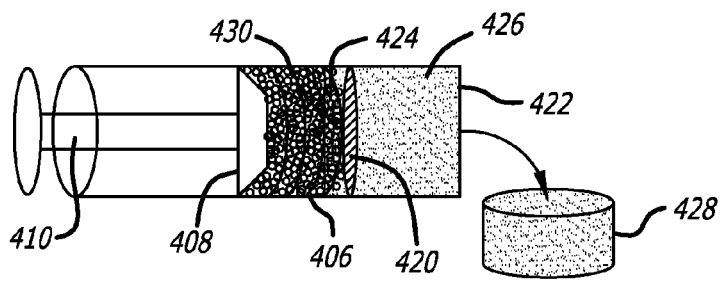

In FIG. 4C, as plunger 408 can be pushed toward distal end 422, the harvested adipose tissue and lipoaspirate move toward filter 420 in second replaceable unit 418. Filter 420 passes lipoaspirate 426 that flows to a collection container 428 near distal end 422 and processed adipose tissue remain 430 on the proximal end 424 of filter 420 with the majority in body portion 406.

Figure 4D:
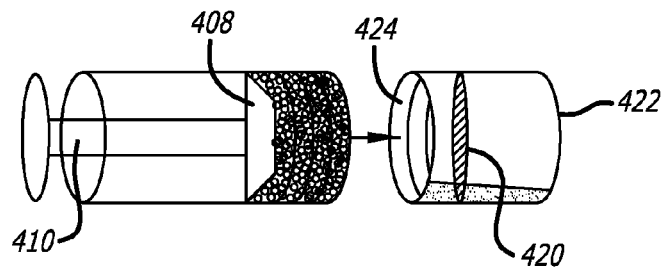

In FIG. 4D, after filtration, second replaceable unit 418 containing filter(s) 420 can be removed with processed adipose tissue 430 remaining in body portion 406.

Figure 4E:
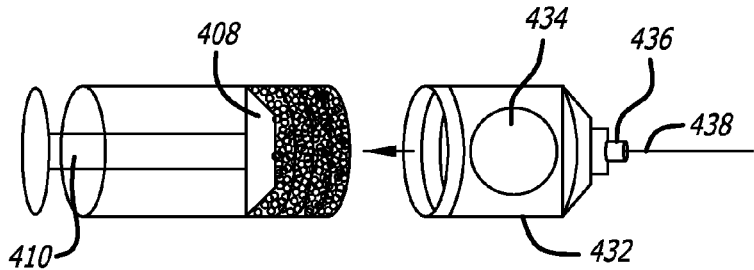

In FIG. 4E, second section 404 is a third replaceable unit 432 containing additive 434 is attached to first section 402. Third replaceable unit 432 can be provided in a package that maintains sterility until it is needed for attachment to first section 402. Distal end 422 can have a luer connection 436 for a needle 438 or cannula that will be used for a fat grafting injection(s).

To mix processed adipose tissue with additive 434, the assembly may be placed in an appropriate orbital mixer or other manual mixing device. Once the proper mix time has elapsed, the injection procedure can commence.

In some embodiments, advantageously, multiple steps for a fat grafting process can be performed with one multi-purpose syringe instead of several different devices. This combining of multiple steps can reduce the duration of the procedure and/or reduce transfer steps of materials.

Syringe Filling Systems

As illustrated in FIG. 5A, a series of syringes 500 is constructed. Each syringe includes in inlet port 502, an outlet port 504 including a luer connector, a body portion 506 for housing harvested adipose tissue, and a plunger 508 for pushing substance out of the body portion 506 through the outlet port 504. A series of two or more syringes can be connected to each other at the end of a harvesting/processing system in order to be filled with harvested adipose tissue.

In one embodiment, illustrated in FIG. 5A, a first syringe 510 is connected to a processing line output 512 at inlet port 502. The output port 504 of first syringe 510 is connected to an inlet port on second syringe 514. The outlet port on second syringe 514 is connected to the inlet port on a third syringe 516. The outlet port on third syringe 516 is connected to the inlet port on a fourth syringe 518. The outlet port of fourth syringe 518 can be connected to a subsequent syringe and so on, or can be the termination of the line of syringes.

In other embodiments, inlet ports of a series of syringes can be connected to a supply line fed from processing line output 512. This way many syringes can be filled at the same time.

In one embodiment, syringes can be single barrel syringes and contain a predetermined amount of additive distributed, for example, in a ribbon, along the length of its body portion. As adipose tissue are introduced into the body portion through the inlet port, the cells mix with the additive.

In another embodiment, as illustrated in FIG. 5B, additives can be located in a second barrel 520 located adjacent to body portion 506. The additive can be mixed with the adipose tissue via a mixing tip 522 just prior to injection through a needle or cannula attached to luer 524.

Mixing tip 522 can include a tortuous path. Tortuous path can be of any configuration that provides mixing of adipose tissue and additives. For example, torturous path can have one, two, three, four, five, six, seven, eight, nine, ten, eleven, twelve, more than two, more than three, more than four, more than five, more than six, more than seven, more than eight, more than nine, more than ten, more than eleven, or more than twelve sharp turns. A sharp turn can be a turn of at least 30 degrees, at least 45 degrees, at least 60 degrees, at least 75 degrees, at least 90 degrees, at least 105 degrees, at least 120 degrees, at least 135 degrees, at least 150 degrees, at least 165 degrees, or at least 180 degrees.

Once filled, the filled syringes can then be separated from each other and the fill valves closed. A needle or cannula can then be attached to the outlet port to allow the harvested and processed fat cell product to be injected into a patient.

Dispensing Devices

Dispensing devices are provided including a container such as a flexible, pliable container. In some embodiments, the container is a bag, suitable for containing contents comprising harvested adipose tissue, or compositions including adipose tissue, for injection into the body.

The dispensing devices include a mechanism for manipulating the container to cause dispensing of the container's contents upon manipulation of the mechanism. The mechanism may be disposed at a proximal end of the container and may be structured to force the container contents toward a distal end of the container. The distal end can include a dispensing element configured to enable dispensing of the container contents to a patient.

The bag may be made of a compliant biocompatible plastic which can be rolled, twisted or compressed. Manipulation of the container, for example, by manual or mechanical means, causes the internal effective volume of the container to become reduced, thereby extruding or expelling the contents of the container from the distal dispensing element. The dispensing element may include a suitable outlet, such as a conduit and cannula or needle, or a hub for coupling with a cannula or needle.

An example dispensing device 600 for containing and dispensing adipose tissue for reintroduction into the body is illustrated in FIG. 6A. Dispensing device 600 comprises a container, such as bag 602, mechanism 604 for manipulating bag 602, and a distal element 606 configured to enable dispensing of container contents 608.

Bag 602 may be made of a compliant biocompatible plastic, for example, polyvinyl chloride (PVC), ethylene vinyl acetate (EVA), polypropylene (PP), or any other suitable material. Bag 602 can be transparent or translucent, and/or include a window or other mechanism for enabling viewing of contents 608.

In one embodiment, bag 602 is biocompatible, pliable and flexible, and can be rolled, twisted or compressed.

In some embodiments, bag 602 can have a volume of about 10 mL to about 2,000 mL, about 100 mL to about 1,000 mL, about 50 mL to about 1,000 mL, about 200 mL to about 2,000 mL, about 200 mL to about 1,000 mL, about 500 mL to about 2,000 mL, or about 500 mL to about 1,000 mL. Generally, different sized bags can be used to accommodate different procedures. Large bags, for example, 1,000 mL or greater, may be used for large volume filling applications (e.g. breast augmentation), and small bags, for example, 10 mL, 20 mL, 30 mL, 40 mL or 50 mL can be provided for small volume applications (e.g. facial filling).

Manipulation of bag 602, by manually or mechanically rotating mechanism 604, causes twisting of bag 602 and forcing of contents 608 toward dispensing element 606. Contents 608 are consequently extruded from dispensing element 606.

In one embodiment, dispensing element 606 can provide a container outlet, including a luer connector which is couplable to a cannula or needle 610, which is suitable for introducing contents 608 into a target region of a patient for tissue bulking, augmentation or reconstructive purposes.

An alternative dispensing element is shown in FIG. 6B, which includes a flexible tubing or conduit 612 coupled between bag 602 and luer connector. Tubing or conduit 612 may be a distal extension of bag 602, or may be connected thereto. The alternate dispensing element may allow for enhanced flexibility and ergonomic grip of cannula or needle 610.

Cannula or needle 610 can be a 10, 12, 14, 16, 18, 20, 22 up to 33 gauge, or other gauges suitable for fat grafting purposes. In one embodiment, the needle gauge is between 10 and 33. The length of needle 610 can be any appropriate length known in the art. A preferred length is about 1/16 inch to about 3 inches, more preferably about 1/16 inch to about 2 inches. Cannula or needle 610 may be blunt or sharp tipped.

Mechanism 604 can be a ring. The ring may be removable or permanently secured to bag 602. In use, the ring can be used to twist and compress bag 602, for example, from proximal end 614 of bag 602 to distal end 616 of bag 602, so that contents 608 (e.g. adipose tissue, or adipose tissue mixed with an additive) are controllably extruded from cannula/needle 610. The ring can provide a controlled twisting of bag 602, and controlled injection of contents 608 by a physician.

In an alternate embodiment, as illustrated in FIG. 7, bag 602 includes a bar 618 that can function as a twist bar to twist proximal end 614 to compress contents 608. Bar 618 can also be used for or include a squeegee that can slide down bag 602 from proximal end 614 toward distal end 616 to compress contents 608.

Advantageously, in some embodiments, bag 602 may include readable metered markings indicating the volume of contents 608 remaining in bag 602 during the dispensing.

Freshly harvested or processed adipose tissue may be introduced into bag 602 using a syringe, or a conduit directly connected to a liposuction device. An additive to be mixed with the adipose tissue may be present in bag 602 prior to introduction of the adipose tissue, or an additive may be introduced with or after the adipose tissue have been introduced into bag 602.

Prior to use of dispensing device 600, a temporary cap (not illustrated) may be provided on, or may be located in place of, a luer connector.

Bag 602 may be sufficiently pliable and puncture resistant to allow a physician to thoroughly mix adipose tissue with an additive(s) by squeezing, shaking or otherwise manipulating exterior walls of bag 602. The temporary cap may then be removed and replaced by cannula or needle 610 prior to a fat grafting injection procedure.

To perform an injection of contents 608 into the patient's target region, for example, breast, the needle or cannula 610 may be introduced into the target region. Bag 602 can be compressed towards distal end 616 to extrude contents 608 from needle or cannula 610, for example using mechanism 604.

The physician can view contents 608 in bag 602 which can be marked to provide a visual indication of the amount of fat dispensed. Manipulation of mechanism 604 can be accomplished by manual, mechanical, electro-mechanical, and/or pneumatic means.

For manual use, in one embodiment, one hand can perform bag compression while cannula or needle 610 is held with the other hand. Alternatively, bag 602 may be inserted into or coupled to a device with a compression device connected to a mechanical or electro-mechanical or gas pressure feature that will provide the compression action. Such a device may include an inject or trigger button to enable compression on demand. In some embodiments, mechanism 604 is operable by a foot pedal to enable compression on demand, allowing hands-free extrusion of contents 608.

The delivery device can have numerous advantages over traditional fat grafting delivery devices. For example, in some embodiments, the present delivery devices can eliminate the need to transfer fat processed in a bag to an alternative dispensing unit (e.g. syringe) thereby reducing the chance of contamination and saving time that would have been required for fat transfer. The dispensing device further provides controlled dispensing with controlled increments of bag compression.

Example 1

Adipose Tissue Transplant for Breast Defect Correction

This example illustrates the use of compositions, methods, and devices disclosed herein for a breast defect correction.

A 32-year-old woman presented with complaints that the medial portions of her breast implants were visible, which accentuated the "bony" appearance of her sternum. In addition, she felt her breasts were too far apart. Pre-operative evaluation of the person includes routine history and physical examination in addition to thorough informed consent disclosing all relevant risks and benefits of the procedure. The physician evaluating the individual determines that she is a candidate for a soft tissue replacement method using the compositions and methods disclosed herein.

To begin the procedure, adipose tissue is harvested from the woman. The procedure is performed at the individual's bedside. The physician examines the individual's habitus for a suitable site or sites to harvest adipose tissue and selects the lateral and medial thigh regions. The harvested area is injected subcutaneously with a standard tumescent fluid solution containing a saline solution, 0.5% lidocaine, and about 0.001% epinephrine. Using an 11-blade scalpel, a small puncture wound is made in order to transverse the dermis. The blade is turned 360 degrees to complete the wound. A two-holed blunt harvesting cannula (3 mm inner diameter) connected to a vacuum pump at low negative pressure (0.5 atm) is then inserted into the subcutaneous adipose tissue plane. The cannula is then moved throughout the plane to disrupt the connective tissue architecture. The volume of aspirate obtained is about 300 mL. The harvest adipose tissue is processed by centrifugation at 3,000 g for 3 minutes to separate healthy adipocytes and regenerative cells from blood, infiltration fluid and cell debris.

A hyaluronic acid-collagen gel additive is mixed with the processed adipose tissue using a device as illustrated in FIG. 1. The amount of additive added is an amount sufficient to promote formation of a blood supply sufficient to support the transplanted tissue. This composition is then transferred to 3 mL syringes from the outlet ports of device 100. One-holed blunt infiltration cannulas (3 mm inner diameter) are used to place the adipose tissue subcutaneously over the lateral sternum and medial breast bilaterally, 70 mL on the right and 50 mL on the left. The adipose tissue is administered in a tear like fashion to increase the surface area to volume ratio.

The individual is monitored for approximately 7 days. The physician evaluates the engrafted tissue and determines that the engraftment was successful. Both the woman and her physician are satisfied with the results of the procedure. Approximately six months after the procedure, the soft tissue replacement appears to be stable and the breast volume has not decreased to any noticeable degree.

Example 2

Adipose Tissue Transplant for Breast Augmentation

This example illustrates the use of compositions and methods disclosed herein for a breast augmentation.

A 28-year-old woman presented micromastia or breast hypoplasia. Pre-operative evaluation of the person includes routine history and physical examination in addition to thorough informed consent disclosing all relevant risks and benefits of the procedure. The physician evaluating the individual determines that she is a candidate for a soft tissue replacement method using the compositions and methods disclosed herein.

To begin the procedure, adipose tissue is harvested from the woman. The procedure is performed at the individual's bedside. The physician examines the individual's habitus for a suitable site or sites to harvest adipose tissue and selects the lateral and medial thigh regions. Using a 10-blade scalpel, a small puncture wound is made in order to transverse the dermis. The blade is turned 360 degrees to complete the wound. A two-holed blunt harvesting cannula (3 mm inner diameter) connected to a syringe is then inserted into the subcutaneous adipose tissue plane. The cannula is then moved throughout the plane to disrupt the connective tissue architecture. The volume of aspirate obtained is about 600 mL. The harvest adipose tissue is processed by centrifugation at 2,700 g for 5 minutes to separate healthy adipocytes and regenerative cells from blood, infiltration fluid and cell debris. The centrifuged adipose tissue is then washed once in a Ringer's saline solution with lactone.

A hyaluronic acid-collagen gel additive is loaded into a first chamber of a device as illustrated in FIG. 2 and the processed adipose tissue is loaded into a second compartment of a device as illustrated in FIG. 2. The amount of additive used is an amount sufficient to promote formation of a blood supply sufficient to support the transplanted tissue. A one-holed blunt infiltration cannula (3 mm inner diameter) is attached to the device in FIG. 2 and the components are mixed and the device is used to place the mixture subcutaneously using axillary, periareolar, and inframammary routes bilaterally, 190 mL on the right and 245 mL on the left. The mixture is administered in a tear like fashion to increase the surface area to volume ratio.

The individual is monitored for approximately 7 days. The physician evaluates the engrafted tissue and determines that the engraftment was successful. Both the woman and her physician are satisfied with the results of the procedure.

Example 3

Adipose Tissue Transplant for Breast Disorder

This example illustrates the use of compositions and methods disclosed herein for a breast disorder.

A 49-year-old woman presented with bilateral tuberous breast deformity. Pre-operative evaluation of the person includes routine history and physical examination in addition to thorough informed consent disclosing all relevant risks and benefits of the procedure. The physician evaluating the individual determines that she is a candidate for a soft tissue replacement method using the compositions and methods disclosed herein.

To begin the procedure, adipose tissue is harvested from the woman. The procedure is performed at the individual's bedside. The physician examines the individual's habitus for a suitable site or sites to harvest adipose tissue and selects the abdomen, buttock, lateral and medial thigh, and trochanter regions. Using a 12-blade scalpel, a small puncture wound is made in order to transverse the dermis. The blade is turned 360 degrees to complete the wound. A two-holed blunt harvesting cannula (3 mm inner diameter) connected to a syringe is then inserted into the subcutaneous adipose tissue plane. The cannula is then moved throughout the plane to disrupt the connective tissue architecture. The volume of aspirate obtained is about 1,400 mL.

The harvested adipose tissue is divided into two, approximately equal portions. One portion is processed by gravity sedimentation to separate healthy adipocytes and regenerative cells from blood, infiltration fluid and cell debris. The other portion is used to isolate regenerative cells. This portion is digested with 0.075% collagenase in buffered saline for 30 minutes on a shaker at 37° C. Regenerative cells are then separated from mature adipocytes and connective tissue by centrifuging at 800 g for 10 minutes. The pellet containing the regenerative cells is then washed three times with buffered saline. The washed regenerative cells are then added back to the sediment purified adipose tissue.

A hyaluronic acid-collagen gel additive made in accordance with methods described herein is mixed with the processed adipose tissue using a system as illustrated in FIG. 4A-E. The amount of additive used is an amount sufficient to promote formation of a blood supply sufficient to support the transplanted tissue. A one-holed blunt infiltration cannula (3 mm inner diameter) is used in combination with the device and the device is used to place the mixture subcutaneously in multiple planes axillary, periareolar, and inframammary routes bilaterally, 380 mL on the right and 370 mL on the left. The mixture is administered in a tear like fashion to increase the surface area to volume ratio.

The individual is monitored for approximately 21 days. The physician evaluates the engrafted tissue and determines that the engraftment was successful. Both the woman and her physician are satisfied with the results of the procedure. Approximately twelve months after the procedure, the woman indicates that her quality of life has improved.

In another instance, the individual is monitored for approximately 7 days. The physician evaluates the engrafted tissue and determines that the engraftment was successful. Both the woman and her physician are satisfied with the results of the procedure because she looked younger. Approximately one month after the procedure, the woman indicates that her quality of life has improved.

Example 4

Adipose Tissue Transplant to Treat Stress Urinary Incontinence

This example illustrates the use of compositions and methods disclosed herein for treating stress urinary incontinence.

A 55-year-old man presents with urinary incontinence. Pre-operative evaluation of the patient includes routine history and physical examination in addition to thorough informed consent disclosing all relevant risks and benefits of the procedure. The physician evaluating the individual determines that he is a candidate for a soft tissue replacement method using the compositions and methods disclosed herein.

To begin the procedure, adipose tissue is harvested from the man. The procedure is performed at the individual's bedside. The physician examines the individual's habitus for a suitable site or sites to harvest adipose tissue and selects the abdomen, and lateral and medial thigh regions. Using a 12-blade scalpel, a small puncture wound is made in order to transverse the dermis. The blade is turned 360 degrees to complete the wound. A two-holed blunt harvesting cannula (3 mm inner diameter) connected to a syringe is then inserted into the subcutaneous adipose tissue plane. The cannula is then moved throughout the plane to disrupt the connective tissue architecture. The volume of aspirate obtained is about 900 mL.

A hyaluronic acid-collagen(I) gel additive is loaded into a first chamber of a device as illustrated in FIG. 2 and the processed adipose tissue is loaded into a second compartment of a device as illustrated in FIG. 2. The amount of additive used is an amount sufficient to promote formation of a blood supply sufficient to support the transplanted tissue. A device as illustrated in FIG. 2 is used to place about 800 mL of adipose tissue transdermally into the bladder neck and proximal urethra regions.

The individual is monitored after the procedure. Approximately three days after the transplant, he experiences a decreased frequency of incontinence. Approximately one month after the procedure, the individual indicates that his quality of life has improved. The physician evaluates the engrafted tissue and determines that the long-term engraftment was successful.

Example 5

Adipose Tissue Transplant for Breast Augmentation

This example illustrates the use of compositions and methods disclosed herein for a breast augmentation.

A 25-year-old woman presented micromastia or breast hypoplasia. Pre-operative evaluation of the person includes routine history and physical examination in addition to thorough informed consent disclosing all relevant risks and benefits of the procedure. The physician evaluating the individual determines that she is a candidate for a soft tissue replacement method using the compositions and methods disclosed herein.

To begin the procedure, adipose tissue is harvested from the woman. The procedure is performed at the individual's bedside. The physician examines the individual's habitus for a suitable site or sites to harvest adipose tissue and selects the lateral and medial thigh regions. Using a 10-blade scalpel, a small puncture wound is made in order to transverse the dermis. The blade is turned 360 degrees to complete the wound. A two-holed blunt harvesting cannula (3 mm inner diameter) connected to a syringe is then inserted into the subcutaneous adipose tissue plane. The cannula is then moved throughout the plane to disrupt the connective tissue architecture. The volume of aspirate obtained is about 600 mL. The harvest adipose tissue is processed by centrifugation at 2,700 g for 5 minutes to separate healthy adipocytes and regenerative cells from blood, infiltration fluid and cell debris. The centrifuged adipose tissue is then washed once in a Ringer's saline solution with lactone.

A hyaluronic acid-collagen gel additive is loaded into a bag as illustrated in FIG. 6A. The processed adipose tissue is also loaded into the bag. The additive and the adipose tissue are mixed together by shaking the bag and massaging them together. The amount of additive used is an amount sufficient to promote formation of a blood supply sufficient to support the transplanted tissue. A one-holed blunt infiltration cannula (3 mm inner diameter) is attached to the device in FIG. 6A and the device is used to place the mixture subcutaneously using axillary, periareolar, and inframammary routes bilaterally, 190 mL on the right and 245 mL on the left. The mixture is administered in a tear like fashion to increase the surface area to volume ratio.

The individual is monitored for approximately 7 days. The physician evaluates the engrafted tissue and determines that the engraftment was successful. Both the woman and her physician are satisfied with the results of the procedure.

Each and every feature of the described systems, methods and uses, and each and every combination of two or more of such features, is included within the scope of the present description provided that the features included in such a combination are not mutually inconsistent.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above-cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

We claim:

1. A system for processing adipose tissue for reintroduction into the body, the system comprising:
    a container including a first compartment, a second compartment, a third compartment, and a tortuous path having a plurality of sharp turns and extending between the second and third compartments, each of the first, second, and third compartments being positioned at different vertical levels of the container to induce movement of harvested adipose tissue by gravity;
    wherein the first compartment is configured to receive and filter the harvested adipose tissue, wherein the second compartment is connected to the first compartment and includes an additive injector, the tortuous path configured to mix and convey additive and fat from the second compartment to the third compartment, and wherein the third compartment is connected to the second compartment via the tortuous path and is configured to dispense adipose tissue and additive to a patient.

2. The system of claim 1, further comprising an additional compartment including the tortuous path connecting the second compartment with the third compartment.

3. The system of claim 1, further comprising a frangible seal separates the first compartment from the second compartment, the seal being breakable by an operator to permit flow from the first compartment to the second compartment.

4. The system of claim 1, further comprising a filter fluidly interconnecting the first compartment with the second compartment to permit flow of harvested adipose tissue therethrough.

5. The system of claim 1, wherein the additive is a hydrogel.

6. The system of claim 1, wherein the additive includes hyaluronic acid.

7. The system of claim 1, wherein the tortuous path extends along a plurality of vertical and horizontal planes interposed between the second and third compartments.

8. The system of claim 1, wherein the second compartment comprises a port for removing processed adipose tissue therefrom.

9. The system of claim 1, wherein the additive injector comprises a port for injecting the additive into the second compartment.

10. The system of claim 1, wherein the additive injector comprises a pouch for dispensing the additive into the second compartment.

11. The system of claim 1, wherein the tortuous path does not vertically overlap with the second or third compartments.

* * * * *

UNITED STATES PATENT AND TRADEMARK OFFICE
CERTIFICATE OF CORRECTION

| | | |
|---|---|---|
| PATENT NO. | : 9,867,939 B2 | |
| APPLICATION NO. | : 14/204796 | |
| DATED | : January 16, 2018 | |
| INVENTOR(S) | : Justin Schwab et al. | |

It is certified that error appears in the above-identified patent and that said Letters Patent is hereby corrected as shown below:

In the Specification

In Column 2, Line 44, delete "the a" and insert -- the --, therefor.

In Column 4, Line 1, delete "any body" and insert -- anybody --, therefor.

In Column 4, Line 20, delete ""allologous"" and insert -- "autologous" --, therefor.

In Column 5, Line 33, delete "abdominus" and insert -- abdominis --, therefor.

In Column 6, Line 15, delete "mesenchyma" and insert -- mesenchymal --, therefor.

In Column 8, Line 9, delete "form" and insert -- from --, therefor.

In Column 10, Lines 48-49, delete "lupis erythematosis)," and insert -- lupus erythematosus), --, therefor.

In Column 10, Line 49, delete "enopthalmos" and insert -- enophthalmos --, therefor.

In Column 10, Line 49, delete "unucleated" and insert -- enucleated --, therefor.

In Column 13, Line 37, delete "amylocalne," and insert -- amylocaine, --, therefor.

In Column 13, Line 41, delete "dimethysoquin," and insert -- dimethisoquin, --, therefor.

In Column 13, Lines 41-42, delete "dycyclonine," and insert -- dicyclomine, --, therefor.

In Column 13, Line 43, delete "formocaine," and insert -- fomocaine, --, therefor.

Signed and Sealed this
Tenth Day of April, 2018

Andrei Iancu
*Director of the United States Patent and Trademark Office*

CERTIFICATE OF CORRECTION (continued)
U.S. Pat. No. 9,867,939 B2

In Column 13, Line 50, delete "psuedococaine," and insert -- pseudococaine, --, therefor.

In Column 24, Line 14, delete "Prilocalne," and insert -- Prilocaine, --, therefor.